(12) United States Patent
Govindan

(10) Patent No.: US 10,280,220 B2
(45) Date of Patent: *May 7, 2019

(54) IMMUNOCONJUGATES WITH AN INTRACELLULARLY-CLEAVABLE LINKAGE

(71) Applicant: Immunomedics, Inc., Morris Plains, NJ (US)

(72) Inventor: Serengulam V. Govindan, Summit, NJ (US)

(73) Assignee: IBC Pharmaceuticals, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/174,304

(22) Filed: Jun. 6, 2016

(65) Prior Publication Data
US 2016/0287722 A1 Oct. 6, 2016

Related U.S. Application Data

(62) Division of application No. 13/921,747, filed on Jun. 19, 2013, now Pat. No. 9,388,237, which is a division of application No. 13/845,694, filed on Mar. 18, 2013, now Pat. No. 9,133,268, which is a division of application No. 13/586,281, filed on Aug. 15, 2012, now Pat. No. 8,425,912, which is a division of application No. 12/512,526, filed on Jul. 30, 2009, now Pat. No. 8,268,319, which is a division of application No. 10/734,589, filed on Dec. 15, 2003, now Pat. No. 7,585,491.

(60) Provisional application No. 60/433,017, filed on Dec. 13, 2002.

(51) Int. Cl.
| | | |
|---|---|---|
| A61K 47/68 | (2017.01) | |
| A61K 47/48 | (2006.01) | |
| C07K 16/28 | (2006.01) | |
| C07K 16/30 | (2006.01) | |
| A61K 45/06 | (2006.01) | |
| C07K 16/18 | (2006.01) | |
| A61K 31/4745 | (2006.01) | |
| A61K 47/60 | (2017.01) | |
| A61K 47/50 | (2017.01) | |

(52) U.S. Cl.
CPC .......... *C07K 16/28* (2013.01); *A61K 31/4745* (2013.01); *A61K 45/06* (2013.01); *A61K 47/60* (2017.08); *A61K 47/6803* (2017.08); *A61K 47/6849* (2017.08); *A61K 47/6889* (2017.08); *C07K 16/18* (2013.01); *C07K 16/2803* (2013.01); *C07K 16/2833* (2013.01); *C07K 16/2851* (2013.01); *C07K 16/30* (2013.01); *A61K 47/50* (2017.08); *C07K 2317/24* (2013.01); *C07K 2317/565* (2013.01); *Y02A 50/401* (2018.01); *Y02A 50/403* (2018.01)

(58) Field of Classification Search
CPC ...................................................... A61K 47/48
USPC ........................................................ 530/391.9
See application file for complete search history.

(56) References Cited

U.S. PATENT DOCUMENTS

| | | | |
|---|---|---|---|
| 4,359,457 A | 11/1982 | Neville et al. | |
| 4,867,962 A * | 9/1989 | Abrams ............ | A61K 51/1054 424/1.49 |
| 5,112,954 A | 5/1992 | Abrams et al. | |
| 5,122,368 A | 6/1992 | Greenfield et al. | |
| 5,708,146 A | 1/1998 | Burrell | |
| 5,824,701 A | 10/1998 | Greenwald et al. | |
| 5,874,540 A * | 2/1999 | Hansen ............ | A61K 47/48576 424/178.1 |
| 6,056,973 A * | 5/2000 | Allen .................... | A61K 9/127 424/450 |
| 6,214,345 B1 | 4/2001 | Firestone et al. | |
| 6,395,276 B1 * | 5/2002 | Rybak .................. | C07K 14/463 424/134.1 |
| 6,716,821 B2 | 4/2004 | Zhao et al. | |
| 7,122,636 B1 | 10/2006 | Hsei et al. | |
| 7,238,785 B2 | 7/2007 | Govindan et al. | |
| 7,312,318 B2 | 12/2007 | Hansen et al. | |
| 7,585,491 B2 | 9/2009 | Govindan et al. | |
| 7,591,994 B2 | 9/2009 | Govindan et al. | |
| 7,999,083 B2 | 8/2011 | Govindan et al. | |
| 8,080,250 B1 | 12/2011 | Govindan et al. | |
| 8,119,101 B2 | 2/2012 | Byrd et al. | |
| 8,268,317 B2 | 9/2012 | Govindan et al. | |
| 8,268,319 B2 * | 9/2012 | Govindan .......... | C07K 16/2803 424/181.1 |
| 8,309,094 B2 | 11/2012 | Gerber et al. | |
| 8,586,049 B2 | 11/2013 | Gerber et al. | |
| 8,759,496 B2 | 6/2014 | Govindan et al. | |

(Continued)

FOREIGN PATENT DOCUMENTS

| | | |
|---|---|---|
| EP | 0253202 | 1/1988 |
| EP | 0253202 | 3/1989 |

(Continued)

OTHER PUBLICATIONS

PubMed Walker et al. (Bioorganic & Medicinal Chemistry Letters, Jan. 21, 2002, 12: 217-219).*

(Continued)

*Primary Examiner* — Yan Xiao
(74) *Attorney, Agent, or Firm* — Richard A. Nakashima

(57) ABSTRACT

The invention relates to therapeutic conjugates with improved ability to target various cancer cells containing a targeting moiety and a therapeutic moiety. The targeting and therapeutic moieties are linked via an acid cleavable linkage that increases therapeutic efficacy of the immunoconjugate.

10 Claims, No Drawings
Specification includes a Sequence Listing.

(56) References Cited

U.S. PATENT DOCUMENTS

| | | | |
|---|---|---|---|
| 8,871,908 B2 | 10/2014 | Liu et al. | |
| 8,877,901 B2 | 11/2014 | Govindan et al. | |
| 8,999,344 B2 | 4/2015 | Govindan et al. | |
| 9,028,833 B2 | 5/2015 | Govindan et al. | |
| 9,102,735 B2 | 8/2015 | Govindan et al. | |
| 9,107,960 B2 | 8/2015 | Govindan et al. | |
| 9,198,978 B2 | 12/2015 | Govindan et al. | |
| 9,388,237 B2* | 7/2016 | Govindan | A61K 47/48715 |
| 10,143,756 B2* | 12/2018 | Govindan | A61K 31/337 |
| 2001/0034363 A1 | 10/2001 | Li et al. | |
| 2003/0133972 A1 | 7/2003 | Danthi et al. | |
| 2005/0180972 A1* | 8/2005 | Wahl | A61K 47/6849 424/144.1 |
| 2012/0052076 A1 | 3/2012 | Alberti | |
| 2013/0089872 A1 | 4/2013 | Nakamura et al. | |
| 2013/0122020 A1 | 5/2013 | Liu et al. | |

FOREIGN PATENT DOCUMENTS

| | | | |
|---|---|---|---|
| WO | 0076551 | 12/2000 | |
| WO | WO 200100245 | * 1/2001 | A61K 47/48 |
| WO | 0124763 | 4/2001 | |
| WO | WO 200174402 | * 10/2001 | A61K 47/48 |
| WO | 2010089782 | 8/2010 | |
| WO | 2003074566 | 9/2013 | |

OTHER PUBLICATIONS

Alberti et al., "Biochemical characterization of Trop-2, a cell surface molecule expressed by human carcinomas: formal proof that the monoclonal antibodies T16 and MOv-16 recognize Trop-2", Hybridoma. Oct. 1992;11(5):539-45.

Bignotti et al., "Trop-2 protein overexpression is an independent marker for predicting disease recurrence in endometrioid endometrial carcinoma", BMC Clin Pathol. Nov. 14, 2012;12:22.

Chang et al., "Ranpimase (frog RNase) targeted with a humanized, internalizing, anti-Trop-2 antibody has potent cytotoxicity against diverse epithelial cancer cells", Mol Cancer Ther. Aug. 2010;9(8):2276-86.

Chen et al., "Increased expression of Trop2 correlates with poor survival in extranodal NK/T cell lymphoma, nasal type", Virchows Arch. Nov. 2013;463(5):713-9.

Cubas et al., "Trop2: a possible therapeutic target for late stage epithelial carcinomas", Biochim Biophys Acta. Dec. 2009;1796(2):309-14.

Fang et al., "Different effects of ERp and TROP2 expression in Chinese patients with early-stage colon cancer", Tumour Biol. Dec. 2012;33(6):2227-35.

Farivar et al., "Nano—drug Delivery of Apoptosis Activator 2 to AGS Cells by Liposomes Conjugated with Anti-TROP2 Antibody", N Am J Med Sci. Nov. 2012;4(11):582-5.

Friedman et al., "BR96 sFv-PE40, a potent single-chain immunotoxin that selectively kills carcinoma cells", Cancer Res. Jan. 15, 1993;53(2)334-9.

Kapoor, S., "TROP2 expression and its evolving role in tumor pathogenesis in systemic tumors", Tumour Biol. Jun. 2013;34(3):1967-8.

Lin et al., "Significantly upregulated TACSTD2 and Cyclin D1 correlate with poor prognosis of invasive ductal breast cancer", Exp Mol Pathol. Feb. 2013;94(1):73-8.

Lin et al., "A novel human Fab antibody for Trop2 inhibits breast cancer growth in vitro and in vivo", Int J Cancer. Mar. 1, 2014;134(5):1239-49.

Lipinski et al., "Human trophoblast cell-surface antigens defined by monoclonal antibodies", Proc Natl Acad Sci U S A. Aug. 1981;78(8):5147-50.

Liu et al., "Overexpression of TROP2 predicts poor prognosis of patients with cervical cancer and promotes the proliferation and invasion of cervical cancer cells by regulating ERK signaling pathway", PLoS One. Sep. 27, 2013;8(9): e75864.

Liu et al., "Trop-2-targeting tetrakis-ranpimase has potent antitumor activity against triple-negative breast cancer", Mol Cancer. Mar. 10, 2014;13:53.

Ning et al., "TROP2 correlates with microvessel density and poor prognosis in hilar cholangiocarcinoma", J Gastrointest Surg. Feb. 2013;17(2):360-8.

Ning et al., "TROP2 expression and its correlation with tumor proliferation and angiogenesis in human gliomas", Neurol Sci. Oct. 2013;34(10):1745-50.

Pak et al., "Significance of EpCAM and TROP2 expression in non-small cell lung cancer", World J Surg Oncol. Apr. 6, 2012;10:53.

Ripani et al., "Human Trop-2 is a tumor-associated calcium signal transducer", Int J Cancer. May 29, 1998;76(5):671-6.

Sapra et al., "Long-term tumor regression induced by an antibody-drug conjugate that targets 5T4, an oncofetal antigen expressed on tumor-initiating cells", Mol Cancer Ther. Jan. 2013;12(1):38-47.

Shi et al., "In vitro and in vivo reactivity of an internalizing antibody, RS7, with human breast cancer", Cancer Res. Dec. 1, 1995;55(23 Suppl):5857s-5863s.

Shor et al., "Enhanced Antitumor Activity of an Anti-5T4 Antibody-Drug Conjugate in Combination with PI3K/mTOR inhibitors or Taxanes", Clin Cancer Res. Jan. 15, 2016;22(2):383-94.

Shvartsur et al., "Trop2 and its overexpression in cancers: regulation and clinical/therapeutic implications", Genes Cancer. Mar. 2015;6(3-4):84-105.

Stein et al., "Radioimmunotherapy of a human lung cancer xenograft with monoclonal antibody RS7: evaluation of (177)Lu and comparison of its efficacy with that of (90)Y and residualizing (131)I", J Nucl Med. Jun. 2001;42(6):967-74.

Stepan et al., "Expression of Trop2 cell surface glycoprotein in normal and tumor tissues: potential implications as a cancer therapeutic target", J Histochem Cytochem. Jul. 2011;59(7):701-10.

Stoyanova et al., "Regulated proteolysis of Trop2 drives epithelial hyperplasia and stem cell self-renewal via β-catenin signaling", Genes Dev. Oct. 15, 2012;26(20):2271-85.

Trerotola et al., "Letter to the editor: efficacy and safety of anti-Trop antibodies, R. Cubas, M. Li, C. Chen and Q. Yao, Biochim Biophys Acta 1796 (2009) 309-1", Biochim Biophys Acta. Apr. 2010;1805(2):119-20.

Tsukahara et al., "TROP2 expressed in the trunk of the ureteric duct regulates branching morphogenesis during kidney development", PLoS One. 2011;6(12):e28607.

Varughese et al., "Cervical carcinomas overexpress human trophoblast cell-surface marker (Trop-2) and are highly sensitive to immunotherapy with hRS7, a humanized monoclonal anti-Trop-2 antibody", Am J Obstet Gynecol. Dec. 2011;205(6):567.e1-7.

Vidmar et al., "Biochemical and preliminary X-ray characterization of the tumor-associated calcium signal transducer 2 (Trop2) ectodomain", Protein Expr Purif. Sep. 2013;91(1):69-76.

Wang et al., "Identification of Trop-2 as an oncogene and an attractive therapeutic target in colon cancers", Mol Cancer Ther. Feb. 2008;7(2):280-5.

Wang et al., "Loss of Trop2 promotes carcinogenesis and features of epithelial to mesenchymal transition in squamous cell carcinoma", Mol Cancer Res. Dec. 2011;9(12):1686-95.

Wu et al., "Potential therapeutic target and independent prognostic marker of TROP2 in laryngeal squamous cell carcinoma", Head Neck. Oct. 2013;35(10):1373-8.

Bardia et al., "Therapy of refractory/relapsed metastatic triple-negative breast cancer (TNBC) with an anti-Trop-2-SN-38 antibody-drug conjugate (ADC), sacituzumab govitecan (IMMU-132): Phase I/II clinical experience", J Clin Oncol 33, 2015 (suppl; abstr 1016), Retrieved from http://meetinglibrary.asco.org/content/150673-156.

Bennouna and Douillard, "Therapeutic strategies for colorectal cancer in Europe and the United States: focus on chemotherapy for advanced colorectal cancer" Int. J. Clin. Oncol. (2002) 7:236-244.

Cao and Suresh, "Bispecific Antibodies as Novel Bioconjugates" Bioconj. Chem. Nov.-Dec. 1998;9(6):635-44.

Cardillo et al., "Humanized anti-Trop-2 IgG-SN-38 conjugate for effective treatment of diverse epithelial cancers: preclinical studies in human cancer xenograft models and monkeys", Clin Cancer Res. May 15, 2011;17(10):3157-69.

(56) References Cited

OTHER PUBLICATIONS

Cardillo et al., "Sacituzumab Govitecan (IMMU-132), an Anti-Trop-2/SN-38 Antibody-Drug Conjugate: Characterization and Efficacy in Pancreatic, Gastric, and Other Cancers", Bioconjug Chem. May 20, 2015;26 (5):919-31, Epub May 8, 2015.
Chari et al., "Immunoconjugates Containing Novel Maytansinoids: Promising Anticancer Drugs" Cancer Res. Jan. 1, 1992;52(1):127-31.
Dotan et al., "A new anti-CEA-SN-38 antibody-drug conjugate (ADC), IMMU-130, is active in controlling metastatic colorectal cancer (mCRC) in patients (pts) refractory or relapsing after irinotecan-containing chemotherapies: Initial results of a phase I/II study", J Clin Oncol 33, 2015 (suppl; abstr 2505), Retrieved from http://meetinglibrary.asco.org/content/148390-156.
Goldenberg et al., "Trop-2 is a novel target for solid cancer therapy with sacituzumab govitecan (IMMU-132), an antibody-drug conjugate (ADC)", Oncotarget. Jun. 18, 2015 [Epub ahead of print].
Govindan et al., "CEACAM5-targeted therapy of human colonic and pancreatic cancer xenografts with potent labetuzumab-SN-38 immunoconjugates", Clin Cancer Res. Oct. 1, 2009;15(19):6052-61.
Govindan et al., "Improving the therapeutic index in cancer therapy by using antibody-drug conjugates designed with a moderately cytotoxic drug", Mol Pharm. Jun. 1, 2015;12(6):1836-47. doi: 10.1021/mp5006195. Epub Nov. 25, 2014.
Govindan et al., "Milatuzumab-SN-38 conjugates for the treatment of CD74+ cancers", Mol Cancer Ther. Jun. 2013;12(6):968-78.
Govindan et al., "IMMU-130, a unique antibody-drug conjugate (ADC) of SN-38 targeting CEACAM5 antigen: Preclinical basis for clinical activity in metastatic colorectal cancer (mCRC)", J Clin Oncol 33, 2015 (suppl 3; abstr 625), Retrieved from http://meetinglibrary.asco.org/content/139777-158.
Guarino et al., "Therapy of advanced metastatic lung cancer with an anti-Trop-2-SN-38 antibody-drug conjugate (ADC), sacituzumab govitecan (IMMU-132): Phase I/II clinical experience", J Clin Oncol 33, 2015 (suppl; abstr 2504), Retrieved from http://meetinglibrary.asco.org/content/148373-156.
Gueritte-Voegelein et al., "Relationships between the Structure of Taxol Analogues and Their Antimitotic Activity" J. Med. Chem. 1991, 34, 992-998.
Guillemard and Saragovi, "Taxane-Antibody Conjugates Afford Potent Cytotoxicity, Enhanced Solubility, and Tumor Target Selectivity" Cancer Res. 61, 694-699, Jan. 15, 2001.
Heindel et al., "A Novel Heterobifunctional Linker for Formyl to Thiol Coupling" Bioconjugate Chem. 1991, 2, 427-430.
King et al., "Monoclonal Antibody Conjugates of Doxorubicin Prepared with Branched Linkers: A Novel Method for Increasing the Potency of Doxorubicin Immunoconjugates" Bioconjugate Chem. 1999, 10, 279-288.
Kreitman et al., "Pseudomonas Exotoxin-based Immunotoxins Containing the Antibody LL2 or LL2-Fab' Induce Regression of Subcutaneous Human B-Cell Lymphoma in Mice" Cancer Res. 53, 819-825, Feb. 15, 1993.
Miller et al., "Development of Taxoids with Enhanced Toxicity and Solubility" Poster Presentation, 224th ACS Nat. Meeting, Aug. 18-22, 2002, Boston, MA.
Newton et al., "Potent and specific antitumor effects of an anti-CD22-targeted cytotoxic ribonuclease: potential for be treatment of non-Hodgkin lymphoma" Blood, 97(2):528-35 (2001).
Okuno et al., "Complete regression of xenografted human carcinomas by camptothecin analogue-carboxymethyl dextran conjugate (T-0128)", Cancer Res. Jun. 1, 2000;60(11):2988-95.
Paul, W., ed., Fundamental Immunology, 3rd Ed., Raven Press, New York, 1993, p. 292-295.
Perez et al., "Inhibition by the anti-mitotic drug doxorubicin of platelet-activating-factor-induced late eosinophil accumulation in rats" Eur. J. Pharmacol. Sep. 4, 1998;356(2-3):239-43.
Robert et al., "Pharmacology of irinotecan", Drugs Today (Baru). Sep. 1998;34(9):777-803.

Rowlinson-Busza and Epenetos, "Targeted delivery of biologic and other antineoplastic agents" Curr. Opin. Oncol. Dec. 1992;4(6):1142-1148.
Sharkey et al., "Combination radioimmunotherapy and chemoimmunotherapy involving different or the same targets improves therapy of human pancreatic carcinoma xenograft models", Mol Cancer Ther. Jun. 2011;10(6):1072-81.
Sharkey et al., "Epratuzumab-SN-38: a new antibody-drug conjugate for the therapy of hematologic malignancies", Mol Cancer Ther. Jan. 2012;11(1):224-34.
Sharkey et al., "Enhanced Delivery of SN-38 to Human Tumor Xenografts with an Anti-Trop-2-SN-38 Antibody Conjugate (Sacituzumab Govitecan)", Clin Cancer Res. Jun. 23, 2015. pii: clincanres.0670.2015. [Epub ahead of print].
Shih et al., "The Processing and Fate of Antibodies and Their Radiolabels Bound to the Surface of Tumor Cells in Vitro: A Comparison of Nine Radiolabels" J. Nucl. Med. 1994; 35:899-908.
Starodub et al., "First-in-Human Trial of a Novel Anti-Trop-2 Antibody-SN-38 Conjugate, Sacituzumab Govitecan, for the Treatment of Diverse Metastatic Solid Tumors", Clin Cancer Res. May 5, 2015. [Epub ahead of print].
Starodub et al., "Phase I/II trial of IMMU-132 (isactuzumab govitecan), an anti-Trop-2-SN-38 antibody drug conjugate (ADC): Results in patients with metastatic gastrointestinal (GI) cancers", J Clin Oncol 33, 2015 (suppl 3; abstr 703), Retrieved from http://meetinglibrary.asco.org/content/140198-158.
Trail et al., "Carcinoma Reactive Doxorubicin (DOX) Conjugates: Comparison of BR64-DOX Conjugates Prepared With Disulfide or Thioether Linkers", Proc. Amer. Assoc. Cancer Res., vol. 34, Mar. 1993, #2858, p. 479.
Walker et al., "Synthesis of an immunoconjugate of camptothecin", Bioorg Med Chem Lett. Jan. 21, 2002;12(2):217-9.
Bardia et al., "Safety and efficacy of anti-Trop-2 antibody drug conjugate, sacituzumab govitecan (IMMU-132), in heavily pretreated patients with TNBC", Poster presented at San Antonio Breast Cancer Symposium, Dec. 10, 2015, San Antonio, TX.
Bardia et al., "Safety and tumor responses of the anti-Trop-2 antibody drug conjugate, sacituzumab govitecan (IMMU-132), in refractory, metastatic, triple-negative breast cancer (TNBC): An ongoing Phase II trial", Poster presented at AACR-NCI-EORTC International Conference: Molecular Targets and Cancer Therapeutics, Nov. 8, 2015, Boston, MA.
Basu et al., "The epithelial/carcinoma antigen EGP-1, recognized by monoclonal antibody RS7-3G11, is phosphorylated on serine 303", Int J Cancer. Aug. 9, 1995;62(4):472-9.
Basu et al., "Epithelial glycoprotein EGP-1 recognized by MAb RS7-3G11 is phosphorylated on serine 303", Proc. Amer. Assoc. Cancer Res. 36: 439 (Abstr. #2621), 1995.
Camidge et al., "Therapy of Advanced Metastatic Lung Cancers with an Anti-Trop-2-SN-38 Antibody-Drug Conjugate, IMMU-132: Interim Phase II Clinical Results", Oral presentation at 16th World Conference on Lung Cancer (WCLC), Sep. 7, 2015, Denver, CO.
Cardillo et al., "A novel immunotoxin comprising quadruple RNase tethered to an internalizing anti-TROP-2 humanized MAb shows potent cytotoxicity against diverse solid tumors in vitro", Proc. Amer. Assoc. Cancer Res. Annual Meeting, 51:1296 (Abstr. #5346), 2010.
Cardillo et al., "Combining an anti-Trop-2 antibody-SN-38 conjugate (sacituzumab govitecan) with microtubule Inhibitors (paclitaxel and eribulin mesylate) or PARP inhibitor (olaparib) significantly improves therapeutic outcome in experimental triple-negative breast cancer (TNBC)", Mol Cancer Ther 2015;14(12 Suppl 2):Abstract nr C166.
Cardillo et al., "Synthetic lethality in TNBC mediated by an anti-Trop-2 antibody-drug conjugate, sacituzumab govitecan (IMMU-132), when combined with paclitaxel or the PARP inhibitor, olaparib", Poster presented at San Antonio Breast Cancer Symposium, Dec. 10, 2015, San Antonio, TX.
Chang et al., "In vitro and in vivo evaluation of a novel recombinant immunotoxin of ranpirnase fused to a humanized anti-EGP-1 antobody, HRS7, for the potential treatment of prostate and lung cancers", Proc. Amer. Assoc. Cancer Res. Annual Meeting, 48: (Abstr. #4795), 2007.

(56) References Cited

OTHER PUBLICATIONS

Goldenberg et al., Tolerability in mice, monkeys, and rabbits of new antibody (MAb)-drug (SN-38) immunoconjugates. Proc. Amer. Assoc. Cancer Res. 102nd Annual Meeting, 52: 865 (Abstr. #3619), 2011.
Goldenberg et al., "SN-38 antibody-drug conjugates as a novel platform for solid cancer therapy: preclinical science", American Association for Cancer Research (AACR) 2014 Annual Meeting, Abstr. #2904, Apr. 7, 2014.
Goldenberg et al., "Characterization of an anti-Trop-2-SN-38 antibody-drug conjugate (IMMU-132) with potent activity against solid cancers", American Society of Clinical Oncology (ASCO) 50th Annual Meeting. J Clin Oncol 32:5s, 2014 (suppl; abstr #3107), 2014.
Goldenberg et al., "IMMU-132, a potential new antibody-drug conjugate (ADC) for the treatment of triple-negative breast cancer (TNBC): Preclinical and initial clinical results", Poster P5-19-08 presented at San Antonio Breast Cancer Symposium, Dec. 9-13, 2014.
Govindan et al., "Optimal cleavable linker for antibody-SN-38 conjugates for cancer therapy: Impact of linker's stability on efficacy", Proc. Amer. Assoc. Cancer Res. 103rd Annual Meeting, 53: 611 (Abstr. #2526), 2012.
Govindan et al., "Preclinical therapy of breast cancer with a radioiodinated humanized anti-EGP-1 monoclonal antibody: advantage of a residualizing iodine radiolabel", Breast Cancer Res Treat. Mar. 2004;84(2):173-82.
Govindan et al., "Conjugation of SN-38 to an anti-EGP-1 MAB, HRS7, via a cleavable linker shows selective therapeutic activity in a preclinical model of non-small cell lung cancer (NSCLC)", Proc. Eleventh Conf. on Cancer Therapy, Cancer Biotherapy & Radiopharmaceuticals, 21(4):401 (Abstr. #56), 2006.
Govindan et al., "Therapy of human colonic and lung cancer xenografts with SN-38 conjugates of anti-CEACAM5 and anti-EGP-1 humanized monoclonal antibodies", Proc. AACR Molecular Targets and Cancer Therapeutics, 347-348 (Abstr. #C287), 2007.
Govindan et al., "Efficacious therapies of two human pancreatic cancer xenografts and an aggressive human lymphoma xenograft with redesigned antibody-SN-38 conjugates", Proc. Amer. Assoc. Cancer Res. Annual Meeting, 51:591 (Abstr. #2438), 2010.
Liu et al., "Novel immunoRNases comprising multiple copies of ranpimase display potent cytotoxicity in human breast cancer cell lines expressing Trop-2", Proc. Amer. Assoc. Cancer Res. 103rd Annual Meeting, 53: 1124 (Abstr. #4636), 2012.
Ocean et al., "Interim results of IMMU-132 (sacituzumab govitecan), an anti-trop-2 antibody-drug conjugate (ADC) in patients with metastatic gastrointestinal (GI) cancers", Poster presented at ESMO's 17th World Congress on Gastrointestinal Cancer, Jul. 4, 2015.
Picozzi et al., "IMMU-132, a new antibody-drug conjugate (ADC), evaluated in patients with advanced, metastatic, pancreatic ductal adenocarcinoma (mPC): Results of a Phase I/II trial", Poster presented at American Association for Cancer Research (AACR) Special Conference on Pancreatic Cancer:Innovations in Research and Treatment, Abstr. #B99, May 18-21, 2014.
Shih et al., "Radioimmunodetection and radioimmunotherapy of xenografted human breast cancer with monoclonal antibody RS7", J. Immunother. 16: 169 (Abstr. #85), 1994.
Starodub et al., "Advanced solid cancer therapy with a novel antibody-drug conjugate (ADC), sacituzumab govitecan (IMMU-132): key preclinical and clinical results", Abstract CT236. Presented at American Association for Cancer Research (AACR) 2015 Annual Meeting, Philadelphia, PA, Apr. 20, 2015.
Starodub et al., "Safety, efficacy, and pharmacokinetics of a new humanized anti-Trop-2 antibody-SN-38 conjugate (IMMU-132) for the treatment of diverse epithelial cancers: Phase I clinical experience", AACR-NCI-EORTC International Conference on Molecular Targets and Cancer Therapeutics Meeting. (Abstr. #C67), Oct. 22, 2013.
Starodub et al., "SN-38 antibody-drug conjugate (ADC) targeting Trop-2, IMMU-132, as a novel platform for the therapy of diverse metastatic solid cancers: Initial clinical results", American Association for Cancer Research (AACR) 2014 Annual Meeting, Abstr. #CT206, Apr. 7, 2014.
Starodub et al., "Therapy of gastrointestinal malignancies with an anti-Trop-2-SN-38 antibody drug conjugate (ADC) (sacituzumab govitecan): Phase I/II clinical experience", 2015 American Society of Clinical Oncology (ASCO) Annual Meeting, J Clin Oncol 33, 2015 (suppl; abstr 3546), Board 38, Jun. 1, 2015.
Stein et al., "Therapy of a breast cancer xenograft using humanized RS7 labeled with residualizing iodine", Proc. Amer. Assoc. Cancer Res. 43: 88 (Abstr. #443), 2002.
Stein et al., "Radioimmunotherapy of lung cancer with MAb RS7-3G11", Proc. Amer. Assoc. Cancer Res. 33: 318 (Abstr. #1897), 1992.
Stein et al., "Radioimmunotherapy with MAb RS7-3G11 in an animal model", Antib. Immunoconj. Radiopharm. 5: 358 (Abstr. #100), 1992.
Stein et al., "Specificity and properties of MAb RS7-3G11 and the antigen defined by this pancarcinoma monoclonal antibody", Int J Cancer. Dec. 2, 1993;55(6):938-46.
Stein et al., "Comparative biodistribution and radioimmunotherapy of monoclonal antibody RS7 and its F(ab')2 in nude mice bearing human tumor xenografts", Cancer. Feb. 1, 1994;73(3 Suppl):816-23.
Stein et al., "Murine monoclonal antibodies raised against human non-small cell carcinoma of the lung: specificity and tumor targeting", Cancer Res. Feb. 15, 1990;50(4):1330-6.
Stein et al., "Effects of radiolabeling monoclonal antibodies with a residualizing iodine radiolabel on the accretion of radioisotope in tumors", Cancer Res. Jul. 15, 1995;55(14):3132-9.
Stein et al., "Successful therapy of a human lung cancer xenograft using MAb RS7 labeled with residualizing radioiodine", Rev Oncol Hematol. Jul.-Aug. 2001;39(1-2):173-80.
Stein et al., "Assessment of combined radioimmunotherapy and chemotherapy for treatment of medullary thyroid cancer", Clin Cancer Res. 5(10 Suppl):3199s-206s, 1999.
Stein et al., Characterization of the epithelial/carcinoma antigen recognized by MAb RS7. Proc. Amer. Assoc. Cancer Res. 35: 501 (Abstr. #2986), 1994.
Stein et al., A novel tumor-associated antigen defined by MAb RS7-3G11: Characterization and internalization properties. Proc. Amer. Assoc. Cancer Res. 33: 341, 1992.
Stein et al., "Characterization of cluster 13: the epithelial/carcinoma antigen recognized by MAb RS7", Int J Cancer Suppl. 1994;8:98-102.
Stein et al., "Targeting and therapy of human non small cell carcinoma of the lung xenografts using 131 I labeled monoclonal antibody RS7 3G11", Proc. Amer. Assoc. Cancer Res. 32: 260, 1991.
Van Rij et al., "Imaging of prostate cancer with immuno-PET and immuno-SPECT using a radiolabeled anti-EGP-1 monoclonal antibody", J Nucl Med. 52(10):1601-7, 2011.
Van Rij et al., "Pretargeting of prostate cancer with an internalizing anti-EGP-1 x anti-HSG bispecific antibody", Annual Congress of the European Association of Nuclear Medicine, Birmingham, UK, Eur J Nucl Med Mol Imaging 38 (Suppl 2):S212 (Abstr. #OP582), 2011.
Vanama et al., Construction, characterization, and mammalian expression of an immunotoxin consisting of ranpimase (Rap) fused to a humanized anti-EGP-1 antibody, hRS7, as a potential therapeutic for prostate cancer. Proc. Amer. Assoc. Cancer Res., 96th Annual Meeting, 160 (Abstr. #679), 2005.
Moon et al., "Antibody conjugates of 7-ethyl-10-hydroxycamptothecin (SN-38) for targeted cancer chemotherapy", J Med Chem. Nov. 13, 2008;51(21):6916-26.

\* cited by examiner

IMMUNOCONJUGATES WITH AN INTRACELLULARLY-CLEAVABLE LINKAGE

This application is a divisional of U.S. patent application Ser. No. 13/921,747, filed Jun. 19, 2013, which was a divisional of U.S. patent application Ser. No. 13/845,694 (now U.S. Pat. No. 9,133,268), filed Mar. 18, 2013, which was a divisional of U.S. patent application Ser. No. 13/586,281 (now U.S. Pat. No. 8,425,912), filed Aug. 15, 2012, which was a divisional of U.S. patent application Ser. No. 12/512,526 (now U.S. Pat. No. 8,268,319), filed Jul. 30, 2009, which was a divisional of U.S. patent application Ser. No. 10/734,589, (now U.S. Pat. No. 7,585,491), filed Dec. 15, 2003, which claimed priority to U.S. Provisional Application No. 60/433,017 filed Dec. 13, 2002, the contents of each of which are incorporated herein by reference in their entirety.

FIELD OF THE INVENTION

The present invention relates to therapeutic conjugates with improved ability to target various cancer cells, infectious disease organisms and for treating autoimmune diseases, which conjugates contain a targeting moiety and a therapeutic moiety. The targeting and therapeutic moieties are linked via an intracellularly cleavable linkage that increases therapeutic efficacy.

BACKGROUND OF THE INVENTION

For many years it has been an aim of scientists in the field of specifically targeted drug therapy to use monoclonal antibodies (mAbs) for the specific delivery of toxic agents to human cancers. Conjugates of tumor-associated mAbs and suitable toxic agents have been developed, but have had mixed success in the therapy of cancer, and virtually no application in other diseases. The toxic agent is most commonly a chemotherapy drug, although particle-emitting radionuclides, or bacterial or plant toxins have also been conjugated to mAbs.

The advantages of using mAb-chemotherapy drug conjugates are that (a) the chemotherapy drug itself is structurally well defined; (b) the chemotherapy drug is linked to the mAb protein using very well defined conjugation chemistries, often at specific sites remote from the mAbs antigen binding regions; (c) mAb-chemotherapy drug conjugates can be made more reproducibly than chemical conjugates involving mAbs and bacterial or plant toxins, and as such are more amenable to commercial development and regulatory approval; and (d) the mAb-chemotherapy drug conjugates are orders of magnitude less toxic than radionuclide mAb conjugates.

Relevant early work on mAb-chemotherapy drug conjugates found during in vitro and in vivo preclinical testing that the chemical linkages used often resulted in the loss of a drug's potency. These results indicated that a drug ideally needed to be released in its original form, once it had been internalized into a target cell, for the mAb-chemotherapy drug conjugate to be a useful therapeutic. Accordingly, work during the 1980's and early 1990's focused largely on the nature of the chemical linker between the chemotherapeutic drug and the mAb. Notably, mAb-chemotherapy drug conjugates prepared using mild acid-cleavable linkers were developed, based on the observation that the pH inside tumors was often lower than normal physiological pH (U.S. Pat. Nos. 4,542,225; 4,569,789; 4,618,492; and 4,952,394).

This approach culminated in a landmark paper by Trail et al. (*Science* 261:212-215 (1993)) which showed that mAb-doxorubicin (DOX) conjugates, prepared with appropriate linkers, could be used to cure mice bearing a variety of human tumor xenografts, in preclinical studies. This promising result was achieved with an antibody that bound to a very large number of receptors on the tumor cells being targeted, and the mAb-chemotherapy drug conjugate was substituted with six to eight DOX residues per unit of mAb. Further, the mAb-chemotherapy drug conjugate was given in massive doses on a repeated dosage schedule.

During the development of the aforementioned mAb-chemotherapy drug conjugates, the linker between the chemotherapeutic drug and the mAb was thought to be critical for retention of good anti-tumor activity both in vitro and in vivo. In some cases, the mAb-chemotherapy drug conjugates were made with acid-labile (e.g., hydrazone) and reductively labile (e.g., disulfide) bonds between the chemotherapy drugs and the mAb. While the hydrazone bond is apparently stable to in vivo serum conditions, normal disulfide bonds were found to be not stable enough for practical use. Accordingly, mAb-chemotherapy drug conjugates were developed that replaced a standard disulfide linkage with a hindered geminal dimethyl disulfide linkage or a methyl disulfide linkage.

Other work in the field has focused on the use of a hydrazone as the cleavable moiety and a thioether group instead of a disulfide linkage. Willner et al. have found superior results by incorporating a hydrazone as a cleavable unit, and attaching DOX to a mAb via a thioether group, instead of a disulfide (U.S. Pat. No. 5,708,146). When linked in such a manner, and using a branched linker capable of doubling the number of DOX units per mAb substitution site, an approximate order of magnitude increase in the efficacy of the new DOX-mAb conjugates was obtained (King et al., *Bioconjugate Chem.* 10:279-288 (1999)).

Another cleavable moiety that has been explored is an ester linkage incorporated into the linker between the antibody and the chemotherapy drug. Gillimard and Saragovi have found that when an ester of paclitaxel was conjugated to anti-rat p75 mAb, MC192, or anti-human TrkA mAb, 5C3, the conjugate was found to exhibit target specific-toxicity. Gillimard and Saragovi, *Cancer Res.* 61:694-699 (2001).

Realizing the importance of the linkers in the construction of mAb-chemotherapy drug conjugates, the inventors have developed novel linkers which may be used generally with a variety of chemotherapeutic drugs and other toxic agents.

SUMMARY OF THE INVENTION

In one embodiment, the invention relates to an immunoconjugate comprising:
  (a) a targeting moiety;
  (b) a chemotherapeutic moiety; and
  (c) a linker binding to the targeting moiety via a thiol group, and to the chemotherapeutic moiety via an intracellularly-cleavable moiety other than a hydrazone. In another embodiment, the invention relates to an immunoconjugate comprising:
  (a) targeting moiety;
  (b) a chemotherapeutic moiety; and
  (c) a linker binding to the targeting moiety via a thiol group, and to the chemotherapeutic moiety via an intracellularly-cleavable moiety other than a hydrazone; wherein said linker comprises an amino acid moiety and a thiol-reactive moiety and is linked to the chemotherapeutic moiety via the amino acid moiety and to the targeting moiety via the thiol-reactive moiety.

Another embodiment of the invention is a method of treating cancer, a malignancy, an autoimmune disease, an infection, or an infectious lesion with the immunoconjugates described herein.

DETAILED DESCRIPTION OF THE PREFERRED EMBODIMENTS

Unless otherwise specified, "a" or "an" means "one or more."

In the description that follows, a number of terms are used and the following definitions are provided to facilitate understanding of the present invention.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as F(ab')$_2$, F(ab)$_2$, Fab', Fab, Fv, scFv (single chain Fv) and the like. Regardless of structure, an antibody fragment binds with the same antigen that is recognized by the intact antibody.

The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region. The Fv fragments may be constructed in different ways as to yield multivalent and/or multispecific binding forms. In the former case of multivalent, they react with more than one binding site against the specific epitope, whereas with multispecific forms, more than one epitope (either of the antigen or even against the specific antigen and a different antigen) is bound.

As used herein, the term antibody component includes both an entire antibody, a fusion protein, and fragments thereof.

A naked antibody is generally an entire antibody which is not conjugated to a therapeutic agent. This is so because the Fc portion of the antibody molecule provides effector or immunological functions, such as complement fixation and ADCC (antibody dependent cell cytotoxicity), which set mechanisms into action that may result in cell lysis. However, the Fc portion may not be required for therapeutic function of the antibody, but rather other mechanisms, such as apoptosis, anti-angiogenesis, anti-metastatic activity, anti-adhesion activity, such as inhibition of heterotypic or homotypic adhesion, and interference in signaling pathways, may come into play and interfere with the disease progression. Naked antibodies include both polyclonal and monoclonal antibodies, and fragments thereof, that include murine antibodies, as well as certain recombinant antibodies, such as chimeric, humanized or human antibodies and fragments thereof. As defined in the present invention, "naked" is synonymous with "unconjugated," and means not linked or conjugated to the therapeutic agent with which it administered.

A chimeric antibody is a recombinant protein that contains the variable domains of both the heavy and light antibody chains, including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, is transferred from the heavy and light variable chains of the rodent antibody into human heavy and light variable domains. The constant domains of the antibody molecule is derived from those of a human antibody.

A human antibody is an antibody obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See for example, McCafferty et al., *Nature* 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, *Current Opiniion in Structural Biology* 3:5564-571 (1993).

Human antibodies may also be generated by in vitro activated B cells. See U.S. Pat. Nos. 5,567,610 and 5,229,275, which are incorporated in their entirety by reference.

A therapeutic agent is a molecule or atom which is administered separately, concurrently or sequentially with an antibody component, i.e., an antibody or antibody fragment, or a subfragment thereof, and is useful in the treatment of a disease. Examples of therapeutic agents include antibodies, antibody fragments, immunoconjugates, drugs, cytotoxic agents, toxins, nucleases, hormones, immunomodulators, chelators, boron compounds, photoactive agents or dyes, radioisotopes or radionuclides, immunoconjugates or combinations thereof.

An immunoconjugate is an antibody component conjugated to a therapeutic agent. Suitable therapeutic agents are described above.

As used herein, the term antibody fusion protein is a recombinantly-produced antigen-binding molecule in which two or more of the same or different natural antibody, single-chain antibody or antibody fragment segments with the same or different specificities are linked. A fusion protein comprises at least one specific binding site.

Valency of the fusion protein indicates the total number of binding arms or sites the fusion protein has to antigen(s) or epitope(s); i.e., monovalent, bivalent, trivalent or mutlivalent. The multivalency of the antibody fusion protein means that it can take advantage of multiple interactions in binding to an antigen, thus increasing the avidity of binding to the antigen, or to different antigens. Specificity indicates how many different types of antigen or epitope an antibody fusion protein is able to bind; i.e., monospecific, bispecific, trispecific, multispecific. Using these definitions, a natural antibody, e.g., an IgG, is bivalent because it has two binding arms but is monospecific because it binds to one type of antigen or epitope. A monospecific, multivalent fusion protein has more than one binding site for the same antigen or epitope. For example, a monospecific diabody is a fusion protein with two binding sites reactive with the same antigen. The fusion protein may comprise a multivalent or multispecific combination of different antibody components or multiple copies of the same antibody component. The fusion protein may additionally comprise a therapeutic agent.

An immunomodulator is a therapeutic agent as defined in the present invention that when present, alters, suppresses or stimulates the body's immune system. Typically, the immunomodulator useful in the present invention stimulates immune cells to proliferate or become activated in an immune response cascade, such as macrophages, B-cells, and/or T-cells. An example of an immunomodulator as described herein is a cytokine, which is a soluble small protein of approximately 5-20 kDs that are released by one cell population (e.g., primed T-lymphocytes) on contact with specific antigens, and which act as intercellular mediators between cells. As the skilled artisan will understand, examples of cytokines include lymphokines, monokines, interleukins, and several related signalling molecules, such as tumor necrosis factor (TNF) and interferons. Chemokines are a subset of cytokines. Certain interleukins and interferons are examples of cytokines that stimulate T cell or other immune cell proliferation.

In a preferred embodiment, the intracellularly-cleavable moiety is optionally cleavable by intracellular esterases. In a preferred embodiment, the intracellularly-cleavable moiety is an ester moiety. In a preferred embodiment, the ester moiety is the ester formed from the α-carboxylic acid of an amino acid. In a preferred embodiment, the intracellularly-cleavable moiety comprises a peptide bond cleavable by intracellular enzymes. In a preferred embodiment, the linker comprises a thiol-reactive group which links to thiol groups of said targeting moiety. The thiol-reactive group is optionally a maleimide or vinylsulfone which links to thiol groups of said targeting moiety. In a preferred embodiment, the linker comprises a thiol group which reacts with a maleimide residue at a lysine side chain of said targeting moiety. The immunoconjugate preferably further comprises an aminopolycarboxylate residue between the chemotherapetic moiety and the targeting moiety. The aminopolycarboxylate is preferably selected from the group consisting of DTPA (diethylenetriaminepentaacetic acid), EDTA (ethylenediaminetetraacetic acid), TTHA (triethylenetetraminehexaacetic acid), benzyl-DTPA, DOTA (1,4,7,10-tetraazacyclododecane-N,N',N'',N'''-tetraacetic acid), benzyl-DOTA, NOTA (1,4,7-triazacyclononane-N,N',N''-triacetic acid), benzyl-NOTA and TETA (1,4,8,11-tetraazacyclotetradecane-1,4,8,11-tetraacetic acid).

The chemotherapeutic moiety is preferably selected from the group consisting of doxorubicin (DOX), epirubicin, morpholinodoxorubicin (morpholino-DOX), cyanomorpholino-doxorubicin (cyanomorpholino-DOX), 2-pyrrolino-doxorubicin (2-PDOX), camptothecin (CPT), irinotecan (CPT-11), SN-38 (the active drug which is metabolically produced, in vivo, from the prodrug CPT-11), topotecan, taxanes, geldanamycin, ansamycins, and epothilones. Targeting moiety is a monoclonal antibody (mAb).

In one embodiment, the targeting moiety is a monoclonal antibody (mAb). In a further embodiment, the targeting moiety may be a multivalent and/or multispecific mAb. The targeting moiety may be a murine, chimeric, humanized, or human monoclonal antibody, and said antibody is in intact, fragment (Fab, Fab', F(ab)$_2$, F(ab')$_2$), or sub-fragment (single-chain constructs) form.

In a preferred embodiment, the targeting moiety is a monoclonal antibody that is reactive with an antigen or epitope of an antigen expressed on a cancer or malignant cell. The cancer cell is preferably a cell from a hematopoietic tumor, carcinoma, sarcoma, melanoma or a glial tumor.

The targeting moiety preferably links to at least one chemotherapeutic moiety, more preferably it links to about 7 to 12 said chemotherapeutic moieties. A preferred linker has the formula:

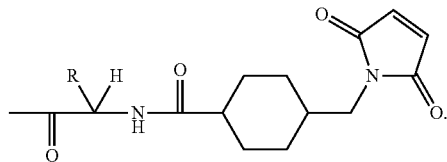

The linker optionally comprises a functional group at the N-terminus, a water-solubilizing moiety at the C-terminus, and one or more internal basic amino acids with side chains available for attachment to said chemotherapeutic moiety. The water-solubilizing moiety is optionally DTPA, EDTA, TTHA, benzyl-DTPA, DOTA, benzyl-DOTA, NOTA, benzyl-NOTA, or N,N'-dialkyl substituted piperazine. The functional group is optionally a thiol-reactive or an amine-reactive group.

The preferred chemotherapeutic moiety is selected from the group consisting of doxorubicin (DOX), epirubicin, morpholinodoxorubicin (morpholino-DOX), cyanomorpholino-doxorubicin (cyanomorpholino-DOX), 2-pyrrolino-doxorubicin (2-PDOX), CPT, CPT-11, SN-38, topotecan, taxanes, geldanamycin, ansamycins, and epothilones.

The immunoconjugates may be used to treat a variety of diseases and conditions, including cancer, malignancies and infectious lesions. A preferred malignancy to be treated according to the present invention is a malignant solid tumor or hematopoietic neoplasm. A preferred target of the immunoconjugate when the method is directed to treatment of an infectious lesion is antigen or epitope or iron-siderophore chelate receptor on a pathogen. The pathogen is preferably selected from the group consisting of a bacterium, fungus, virus, rickettsia, mycoplasma and protozoa. In particular, the pathogen may be selected from the group consisting of *Streptococcus agalactiae, Legionella pneumophilia, Streptococcus pyogenes, Escherichia coli, Neisseria gonorrhosae, Neisseria meningitidis, Pneumococcus, Hemophilis influenzae B, Treponema pallidum, Lyme disease spirochetes, Pseudomonas aeruginosa, Mycobacterium leprae, Brucella abortus*, mycobacterium tuberculosis, rabies virus, influenza virus, cytomegalovirus, herpes simplex virus I, herpes simplex virus II, human serum parvo-like virus, respiratory syncytial virus, varicella-zoster virus, hepatitis B virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reo virus, polio virus, simian virus 40, mouse mammary tumor virus, dengue virus, rubella virus, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M salivarium* and *M. pneumoniae*.

The immunoconjugates may also be used to treat autoimmune disease, including class III autoimmune diseases. Preferred class III autoimmune diseases for treatment according to the invention are selected from the group consisting of immune-mediated thrombocytopenias, dermatomyositis, Sjögren's syndrome, multiple sclerosis, Sydenham's chorea, myasthenia gravis, systemic lupus erythematosus, lupus nephritis, rheumatic fever, rheumatoid arthritis, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis ubiterans, primary biliary cirrhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis.

The immunoconguates are preferably administered parenterally.

In one aspect of the preferred embodiments of the present invention, the invention relates to an immunoconjugate comprising a targeting moiety, a chemotherapeutic moiety and a linker binding to the targeting moiety via a thiol group, and to the chemotherapeutic moiety via an intracellularly-cleavable moiety other than a hydrazone.

In a preferred embodiment, the intracellularly-cleavable moiety other than a hydrazone are moieties that may be cleaved once internalized into the cell to which the mAb recognizes and binds to a receptor, and particularly cleaved by esterases and amidases.

In a preferred embodiment, the chemotherapeutic moiety is separately activated at neutral pH such that it contains a thiol-reactive group. It is within the skill of the ordinary skilled artisan to develop chemistries that would allow for the incorporation of thiol-reactive groups into any chemotheraputic moiety. In a preferred embodiment, however, the chemotherapeutic moiety may be activated such that the group bearing the thiol-reactive group is spaced from the chemotherapeutic moiety by an amino acid radical. In a preferred embodiment, the α-amino group of the amino acid may reacted with a reagent bearing a thiol-reactive group, such as maleimide, chloroacetamide, bromoacetamide, iodoacetamide, and vinylsulfone. Preferably, said reagent bearing a thiol-reactive group is succinimidyl [4-maleimidomethyl]cyclohexane-1-carboxylate (SMCC). In the case of SMCC, the thiol-reactive group is a maleimide group. The product resulting from the reaction of SMCC and the chemotherapeutic moiety comprising an amino acid radical is the general compound illustrated below:

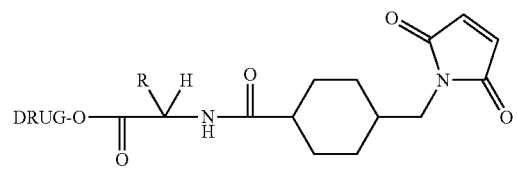

wherein R is the side chain of any amino acid.

While not wishing to be bound by this theory, the maleimido cyclohexyl carboxylate group is thought to be particularly useful in the context of the preferred embodiments of the present invention for two reasons. First, the cyclohexyl group in the linker is thought to stabilize the amide functionality formed from the reaction of SMCC and the amino acid α-amino group. Second, the ester formed between the drug and the amino acid carboxylate is cleaved once the immunoconjugate is internalized into the cell. An example of intracellularly cleaved ester bond is paclitaxel-MC192 immunoconjugate (Gillimard and Saragovi, supra).

In a preferred embodiment of the present invention, the chemotherapeutic moiety comprising an amino acid radical, as shown above, contains the linker; that is, the linker binding to the targeting moiety via a thiol group. The linker is the portion of the molecule shown below:

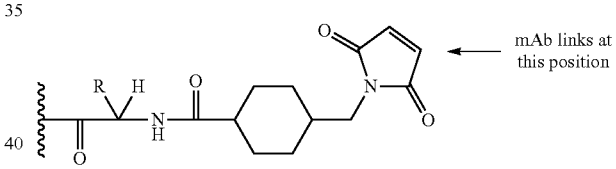

However, the scope of the preferred embodiments of the present invention is not so limited. The linker may be a moiety that simply comprises an amino acid radical and a thiol-reactive group. The amino acid radical and the thiol-reactive group may be spaced by any moieties known to the skilled artisan, including the 4-methylene cyclohexane-1-carbonyl moiety shown above.

The immunoconjugate of the preferred embodiments of the present invention is obtained from the reaction of the activated chemotherapeutic moiety with an antibody using methods well known in the art. The chemotherapeutic moiety may be attached to the mAb through the thiol-reactive group after reduction of the mAb inter-chain disulfide bonds. This approach generates an average of eight free thiol groups per molecule of antibody, and does so in a reproducible manner at the limiting levels of thiol used in the reduction reaction.

For conjugating to lysine groups of an antibody, the antibody is first derivatized to contain a thiol-reactive group, with the chemotherapeutic moiety containing a thiol group. Methods for introducing thiol groups on to antibodies by modifications of mAb's lysine groups are well known in the art (Govindan et al. Bioconjugate Chemistry, 7:290-297, 1996; Wong in *Chemistry of protein conjugation and cross-linking*, CRC Press, Inc., Boca Raton, Fla. (1991), pp 20-22). In this way, the bifunctional chemotherapeutic moiety is conjugated to antibody fragments and subfragments including single-chain constructs. Conversely, the chemotherapeutic moiety contains a thiol-reactive group which reacts with the thiol(s) of a reduced mAb.

The targeting moiety is preferably an antibody (including fully human, non-human, humanized, or chimeric antibodies) or an antibody fragment (including enzymatically or recombinantly produced fragments) and binding proteins incorporating sequences from antibodies or antibody fragments. The antibodies, fragments, and binding proteins may be multivalent and multispecific or multivalent and monospecific as defined above.

In a preferred embodiment of the present invention, antibodies, such as mAbs, are used that recognize or bind to markers or tumor-associated antigens that are expressed at high levels on target cells and that are expressed predominantly or only on diseased cells versus normal tissues, and antibodies that internalize rapidly. Antibodies useful within the scope of the present invention include mAbs with properties as described above (and show distinguishing properties of different levels of internalization into cells and microorganisms), and contemplate the use of, but are not limited to, in cancer, the following mAbs: LL1 (anti-CD74), LL2 (anti-CD22), RS7 (anti-epithelial glycoprotein-1(EGP-1)), PAM-4 and KC4 (both anti-MUC1), MN-14 (anti-carcinoembryonic antigen (CEA, also known as CD66e), Mu-9 (anti-colon-specific antigen-p), Immu 31 (an anti-alpha-fetoprotein), TAG-72 (e.g., CC49), Tn, J591 (anti-PSMA (prostate-specific membrane antigen)), G250 (an anti-carbonic anhydrase IX mAb) and L243 (anti-HLA-DR). Other useful antigens that may be targeted using these conjugates include HER-2/neu, BrE3, CD19, CD20 (e.g., C2B8, hA20, 1F5 Mabs) CD21, CD23, CD80, alpha-fetoprotein (AFP), VEGF, EGF receptor, P1GF, MUC1, MUC2, MUC3, MUC4, PSMA, gangliosides, HCG, EGP-2 (e.g., 17-1A), CD37, HLA-DR, CD30, Ia, A3, A33, Ep-CAM, KS-1, Le(y), 5100, PSA (prostate-specific antigen), tenascin, folate receptor, Thomas-Friedenreich antigens, tumor necrosis antigens, tumor angiogenesis antigens, Ga 733, IL-2, IL-6, T101, MAGE, antigen to which L243 binds, CD66 antigens, i.e. CD66a-d or a combination thereof. The CD66 antigens consist of five different glycoproteins with similar structures, CD66a-e, encoded by the carcinoembryonic antigen (CEA) gene family members, BCG, CGM6, NCA, CGM1 and CEA, respectively. These CD66 antigens are expressed mainly in granulocytes, normal epithelial cells of the digestive tract anc tumor cells of various tissues. A number of the aforementioned antigens are disclosed in U.S. Provisional Application Ser. No. 60/426,379, entitled "Use of Multi-specific, Non-covalent Complexes for Targeted Delivery of Therapeutics," filed Nov. 15, 2002.

In another preferred embodiment of the present invention, antibodies are used that internalize rapidly and are then re-expressed, processed and presented on cell surfaces, enabling continual uptake and accretion of circulating immunoconjugate by the cell. An example of a most-preferred antibody/antigen pair is LL1, an anti-CD74 mAb (invariant chain, class II-specific chaperone, Ii). The CD74 antigen is highly expressed on B-cell lymphomas, certain T-cell lymphomas, melanomas and certain other cancers (Ong et al., *Immunology* 98:296-302 (1999)), as well as certain autoimmune diseases.

The diseases that are preferably treated with anti-CD74 antibodies include, but are not limited to, non-Hodgkin's lymphoma, melanoma and multiple myeloma. Continual expression of the CD74 antigen for short periods of time on the surface of target cells, followed by internalization of the antigen, and re-expression of the antigen, enables the targeting LL1 antibody to be internalized along with any chemotherapeutic moiety it carries as a "payload." This allows a high, and therapeutic, concentration of LL1-chemotherapeutic drug immunoconjugate to be accumulated inside such cells. Internalized LL1-chemotherapeutic drug immunoconjugates are cycled through lysosomes and endosomes, and the chemotherapeutic moiety is released in an active form within the target cells.

In another aspect, the invention relates to a method of treating a subject, comprising administering a therapeutically effective amount of a therapeutic conjugate of the preferred embodiments of the present invention to a subject. Diseases that may be treated the therapeutic conjugates of the preferred embodiments of the present invention include, but are not limited to B-cell malignancies (e.g., non-Hodgkins lymphoma and chronic lymphocytic leukemia using, for example LL2 mAb; see U.S. Pat. No. 6,183,744), adenocarcinomas of endodermally-derived digestive system epithelia, cancers such as breast cancer and non-small cell lung cancer, and other carcinomas, sarcomas, glial tumors, myeloid leukemias, etc. In particular, antibodies against an antigen, e.g., an oncofetal antigen, produced by or associated with a malignant solid tumor or hematopoietic neoplasm, e.g., a gastrointestinal, lung, breast, prostate, ovarian, testicular, brain or lymphatic tumor, a sarcoma or a melanoma, are advantageously used.

As used herein, the term "subject" refers to any animal (i.e., vertebrates and invertebrates) including, but not limited to mammals. The term subject also includes rodents (e.g., mice, rats, and guinea pigs). It is not intended that the term be limited to a particular age or sex. Thus, adult and newborn subjects, as well as fetuses, whether male or female, are encompassed by the term.

In another preferred embodiment, the therapeutic conjugates comprising the Mu-9 mAb of the preferred embodiments of the present invention can be used to treat colorectal, as well as pancreatic and ovarian cancers as disclosed in U.S. application Ser. No. 10/116,116, filed Apr. 5, 2002 and by Gold et al. (*Cancer Res*. 50: 6405 (1990), and references cited therein). In addition, the therapeutic conjugates comprising the PAM-4 mAb of the preferred embodiments of the present invention can be used to treat pancreatic cancer, as disclosed in U.S. Provisional Application Ser. No. 60/388,314, filed Jun. 14, 2002.

In another preferred embodiment, the therapeutic conjugates comprising the RS-7 mAb of the preferred embodiments can be used to treat carcinomas such as carcinomas of the lung, stomach, urinary bladder, breast, ovary, uterus, and prostate, as disclosed in U.S. Provisional Application Ser. No. 60/360,229, filed Mar. 1, 2002 and by Stein et al. (*Cancer Res*. 50: 1330 (1990) and *Antibody Immunoconj. Radiopharm*. 4: 703 (1991)).

In another preferred embodiment, the therapeutic conjugates comprising the anti-AFP mAb of the preferred embodiments can be used to treat hepatocellular carcinoma, germ cell tumors, and other AFP-producing tumors using humanized, chimeric and human antibody forms, as disclosed in U.S. Provisional Application Ser. No. 60/399,707, filed Aug. 1, 2002.

In another preferred embodiment, the therapeutic conjugates comprising anti-tenascin antibodies can be used to treat hematopoietic and solid tumors and conjugates comprising antibodies to Le(y) can be used to treat solid tumors.

In another preferred embodiment, diseases that may be treated using the therapeutic conjugates of the preferred embodiments of the present invention include, but are not limited to immune dysregulation disease and related autoimmune diseases, including Class III autoimmune diseases such as immune-mediated thrombocytopenias, such as acute idiopathic thrombocytopenic purpura and chronic idiopathic thrombocytopenic purpura, dermatomyositis, Sjögren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis ubiterans, Sjogren's syndrome, primary biliary cirrhosis, Hashimoto's thyroiditis, thyrotoxicosis, scleroderma, chronic active hepatitis, rheumatoid arthritis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis, as disclosed in U.S. Provisional application Ser. No. 60/360,259, filed Mar. 1, 2002. Typical antibodies useful in these diseases include, but are not limited to, those reactive with HLA-DR antigens, B-cell antigens (e.g., CD19, CD20, CD21, CD22, CD23, CD4, CD5, CD8, CD14, CD15, CD19, CD20, CD21, CD22, CD23, CD25, CD33, CD37, CD38, CD40, CD40L, CD46, CD52, CD54, CD74, CD80, CD126, B7, MUC1, Ia, HM1.24, and HLA-DR). Since many of these autoimmune diseases are affected by autoantibodies made by aberrant B-cell populations, depletion of these B-cells by therapeutic conjugates involving such antibodies bound with the drugs used in this invention, is a preferred method of autoimmune disease therapy, especially when B-cell antibodies are combined, in certain circumstances, with HLA-DR antibodies and/or T-cell antibodies (including those which target IL-2 as an antigen, such as anti-TAC antibody).

In another preferred embodiment, the therapeutic conjugates of the preferred embodiments can be used against pathogens, since antibodies against pathogens are known. For example, antibodies and antibody fragments which specifically bind markers produced by or associated with infectious lesions, including viral, bacterial, fungal and parasitic infections, for example caused by pathogens such as bacteria, rickettsia, mycoplasma, protozoa, fungi, and viruses, and antigens and products associated with such microorganisms have been disclosed, inter alia, in Hansen et al., U.S. Pat. No. 3,927,193 and Goldenberg U.S. Pat. Nos. 4,331,647, 4,348,376, 4,361,544, 4,468,457, 4,444,744, 4,818,709 and 4,624,846. In a preferred embodiment, the pathogens are selected from the group consisting of *Streptococcus agalactiae*, *Legionella pneumophilia*, *Streptococcus pyogenes*, *Escherichia coli*, *Neisseria gonorrhosae*, *Neisseria meningitidis*, *Pneumococcus*, *Hemophilis influenzae B*, *Treponema pallidum*, Lyme disease spirochetes, *Pseudomonas aeruginosa*, *Mycobacterium leprae*, *Brucella abortus*, *mycobacterium* tuberculosis, rabies virus, influenza virus, cytomegalovirus, herpes simplex virus I, herpes simplex virus II, human serum parvo-like virus, respiratory syncytial virus, varicella-zoster virus, hepatitis B virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reo virus, polio virus, simian virus 40, mouse mammary tumor virus, dengue virus, rubella virus, *Plasmodium falciparum*, *Plasmodium vivax*, *Toxoplasma gondii*, *Trypanosoma rangeli*, *Trypanosoma cruzi*, *Trypanosoma rhodesiensei*, *Trypanosoma brucei*, *Schistosoma mansoni*, *Schistosoma japanicum*, *Babesia bovis*, *Elmeria tenella*, *Onchocerca volvulus*, *Leishmania tropica*, *Trichinella spiralis*, *Theileria parva*, *Taenia hydatigena*, *Taenia ovis*, *Taenia saginata*, *Echinococcus granulosus*, *Mesocestoides corti*, *Mycoplasma arthritidis*, *M. hyorhinis*, *M. orate*, *M. arginini*, *Acholeplasma laidlawii*, *M. salivarium* and *M. pneumoniae*, as disclosed in U.S. Pat. No. 6,440,416.

In one embodiment, antibiotics are delivered as chemoconjugates incorporating siderophore components for use against infection with Gram-negative bacterial pathogens. Siderophores are iron-chelating bis catecholates of di- or triamines, and are used as delivery vehicles. The iron chelate of siderophores are recognized by specific receptors on the bacterial membrane, thus leading to active transport inside the bacterila cell (Heinisch et al. J. Medicinal Chemistry, 45: 3032-3040, 2002). Within the context of the present invention, a peptide is assembled with protected lysine as the N-terminus. The carboxyl end of the peptide, liberated from the resin support, is then activated, and coupled to amine-containing antibiotic such as penicillin N. The protecting groups at the N-terminus are cleaved, and the amino groups of the N-terminal lysine are then conjugated to 2,3-diacetoxybenzoyl chloride to ultimately furnish the required bis catecholate-appended penicillin conjugate. The diacetyl derivative of the catechol moiety is also effective as siderophore component (Heinisch et al. supra).

In a preferred embodiment, the antibodies that are used in the treatment of human disease are human or humanized (CDR-grafted) versions of antibodies; although murine and chimeric versions of antibodies can be used. For veterinary uses, the same-species IgG would likely be the most effective vector, although cross-species IgGs would remain useful. Same species IgG molecules as delivery agents are mostly preferred to minimize immune responses. This is particularly important when considering repeat treatments. For humans, a human or humanized IgG antibody is less likely to generate an anti-IgG immune response from patients. Targeting an internalizing antigen, antibodies such as hLL1 and hLL2 rapidly internalize after binding to target cells, which means that the chemotherapeutic drug being carried is rapidly internalized into cells. However, antibodies that have slower rates of internalization can also be used to effect selective therapy with this invention.

In a preferred embodiment of this invention, a more effective incorporation into cells and pathogens can be accomplished by using multivalent, multispecific or multivalent, monospecific antibodies. Multivalent means the use of several binding arms against the same or different antigen or epitope expressed on the cells, whereas multispecific antibodies involve the use of multiple binding arms to target at least two different antigens or epitopes contained on the targeted cell or pathogen. Examples of such bivalent and bispecific antibodies are found in U.S. patent applications 60/399,707, filed Aug. 1, 2002; 60/360,229, filed Mar. 1, 2002; 60/388,314, filed Jun. 14, 2002; and Ser. No. 10/116, 116, filed Apr. 5, 2002, all of which are incorporated by reference herein.

In a preferred embodiment of the present invention, camptothecin (CPT) and its derivatives are preferred chemotherapeutic moieties, although the invention is not so limited. Other chemotherapeutic moieties that are within the scope of the invention are taxanes (e.g, baccatin III, taxol), epothilones, anthracycline drugs (doxorubicin (DOX), epirubicin, morpholinodoxorubicin (morpholino-DOX), cyanomorpholino-doxorubicin (cyanomorpholino-DOX), and 2-pyrrolinodoxorubicin (2-PDOX); see Priebe W (ed.), ACS symposium series 574, published by American Chemical Society, Washington D.C., 1995. (332 pp) and Nagy et al., *Proc. Natl. Acad. Sci. USA* 93:2464-2469, 1996), benzoquinoid ansamycins exemplified by geldanamycin (DeBoer et al., *Journal of Antibiotics* 23:442-447, 1970; Neckers et al., *Invest. New Drugs* 17:361-373, 1999), and the like. Preferably, in the immunoconjugates of the preferred embodiments of the present invention, the targeting moiety links to at least one chemotherapeutic moiety; preferably 1 to about 5 chemotherapeutic moieties; most preferably about 7 to about 12 chemotherapeutic moieties.

CPT derivatives are a class of potent antitumor agents. Irinotecan (also referred to as CPT-11) and topotecan are CPT analogs which are approved cancer therapeutics (Iyer and Ratain, *Cancer Chemother. Phamacol.* 42: S31-S43 (1998)). CPTs act by inhibiting topoisomerase I enzyme by stabilizing topoisomerase I-DNA complex (Liu, et al. in *The Camptothecins: Unfolding Their Anticancer Potential*, Liehr J. G., Giovanella, B. C. and Verschraegen (eds), NY Acad. Sci., NY (2000), pp 1-10).

CPTs present a set of caveats in the preparation of immunoconjugates. One caveat is the insolubility of most CPT derivatives in aqueous buffers. Secondly, CPTs provide very few options for structural modification for conjugating to macromolecules. For instance, CPT itself contains only a tertiary hydroxyl group in ring-E. The hydroxyl functional group in the case of CPT must be coupled to a linker suitable for subsequent protein conjugation. Thirdly the lability of the δ-lactone moiety of the E-ring of their structures, under physiological conditions, results in greatly reduced antitumor potency of these products. Therefore, the conjugation protocol is performed such that it is carried out at a pH of 7 or lower to avoid the lactone ring opening. Typically conjugation of a bifunctional CPT possessing an amine-reactive group such as an active ester would require a pH of 8 or greater. Fourth, an intracellularly-cleavable moiety is to be incorporated in the linker/spacer connecting the CPTs and the antibodies.

The problem of δ-lactone opening under physiological conditions has been previously addressed. One approach has been to acylate the C-20 hydroxyl group with an amino acid, and couple the α-amino group of the amino acid to poly-L-glutamic acid. This approach relies on the passive diffusion of a polymeric molecule into tumor sites. This glycine conjugation has also been reported as a method of making water-soluble derivative of CPT (U.S. Pat. No. 4,943,579) and in the preparation of a PEG-derivatization of CPT (Greenwald, et al. *J. Med. Chem.* 39: 1938-1940 (1996). In the latter case, the approach has been devised in the context of developing water-soluble and long acting forms of CPT, whereby CPT's in vivo half-life is enhanced, and the drug is gradually released from its conjugate while in circulation in vivo.

In a preferred embodiment, the present invention devises methods for preparing immunoconjugates of CPTs, taking into consideration the four caveats described above. The preferred embodiments of the present invention address the caveats in the following ways. First, the water-solubility of CPT is increased by placing an aminopolycarboxylate between the chemotherapeutic moiety (i.e., CPT) and the antibody. In a preferred embodiment the aminopolycarboxylate is selected from the group consisting of DTPA (diethylenetriaminepentaacetic acid), NOTA (1,4,7-triazacyclononane-N,N',N''-triacetic acid), DOTA (1,4,7,10-tetraazacyclododecane-N,N',N'',N'''-tetraacetic acid), and TETA (1,4,8,11-tetraazacyclotetradecane-1,4,8,11-tetraacetic acid).

In a preferred embodiment, the aminopolycarboxylate is DTPA. In a particularly preferred embodiment, the DTPA is attached to the chemotherapeutic moiety by way of a reagent bearing the same. Preferably, said reagent bearing an aminopolycarboxylate is:

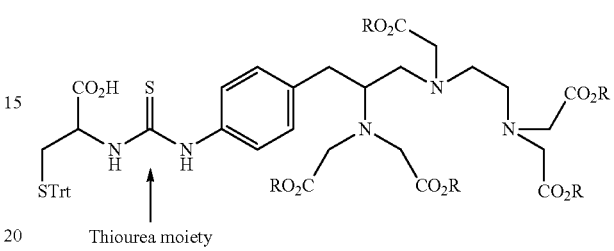

Thiourea moiety wherein "Trt" is a trityl group and the R groups on the carboxylates are either hydrogen or alkyl (wherein alkyl means a straight or branched chain $C_1$-$C_6$-alkyl group). The ordinary skilled artisan would be able to develop other reagents bearing an aminopolycarboxylate that would be useful in the practice of the preferred embodiments of the present invention. The reagent bearing a hapten can be attached to the chemotherapeutic moiety via the carboxylic acid of the thiourea moiety by methods well know in the art. One such method well know in the art is described in Example 8. Where R is alkyl, the esters are deprotected to ultimately obtain the corresponding DTPA derivative.

The reagent bearing an aminopolycarboxylate may be attached to the chemotherapeutic moiety directly or by way of an amino acid spacer. In a preferred embodiment, the reagent bearing an aminopolycarboxylate is attached to the chemotherapeutic moiety via a glycine spacer, and more preferably via valine spacer. The use of more hindered valinate ester has been shown to provide a hydrolytically stable moiety (Lerchen H-G et al., *J. Med. Chem.* 44:4186-4195 (2001)). The derivatization of C-20 hydroxyl as an ester can also involve a dipeptide or a polypeptide. When the chemotherapeutic moiety is 10-hydroxy CPT, the glycyl spacer is attached either at the A-ring hydroxyl group or at the C-20 hydroxyl group as shown in Example 7, below; most preferably, the glycyl or other spacers mentioned above is attached at the C-20 hydroxyl group.

In a preferred embodiment, the water-solubility of the chemotherapeutic moiety is increased via the incorporation of the following moiety (A) at a hydroxyl group on the chemotherapeutic moiety:

A

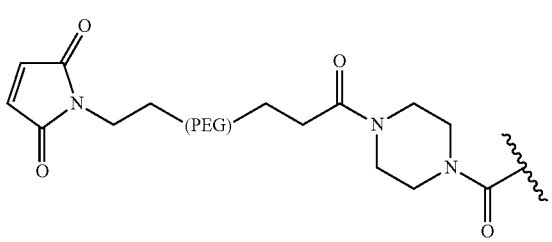

wherein "PEG" denotes polyethylene glycol. This moiety not only increases the water solubility of the chemotherapeutic moiety, but it also incorporates a thiol reactive group. In the case of 10-hydroxy CPT, the aforementioned moiety may be attached at the A-ring hydroxyl group or at the C-20 hydroxyl group.

For attachment to the C-20 hydroxyl, the C-10 hydroxyl is first protected. The C-20 hydroxyl is then converted to, for example, the glycinate ester. At this point, the C-10 hydroxyl may be deprotected. The free amino group of the C-20 glycinate ester can then be suitably elaborated to contain, for example, an intracellularly cleavable 'Phe-Lys' dipeptide linkage which is recognized and cleaved by intracellular Cathepsin B enzyme. The PEG-containing moiety shown above is then installed at the free amino group at the end of the C-20 glycinate-Phe-Lys dipeptide.

Second, the δ-lactone is stabilized via derivatization of the C-20 hydroxyl group with an amino acid radical. The use of an amino acid linker/spacer at the C-20 hydroxyl of CPT is advantageous for further elaboration of the amine with a thiol-reactive moiety. Moreover, the amino acid linker/spacer acts as an intracellularly-cleavable moiety. At this point, the immunoconjugate effectively becomes an intracellularly-activated prodrug. That is, the release of the chemotherapeutic moiety from the immunoconjugate would depend upon the binding of the immunoconjugate to tumor-specific antigens, subsequent internalization, routing to lysosomal compartment, and finally processing of the conjugate by lysosomal enzymes resulting in the release of the drug.

Finally, the conjugation protocol is based on a thiol-maleimide or a thiol-vinylsulfone reaction which is facile at neutral or acidic pH. This obviates the need for higher pH conditions for conjugations as, for instance, would be necessitated when using active esters.

In another aspect, the present invention relates to a modular approach for introducing a water-solubilizing moiety and a thiol-reactive moiety (e.g., maleimide groups) into the immunoconjugates of the preferred embodiments of the present invention. The water-solubilizing moiety and the thiol-reactive moiety are conveniently introduced onto a template such as: MCC-Gly-Lys-Lys(R')—NH$_2$, wherein MCC is 4-maleimidomethyl-cyclohexyl-1-carbonyl (the maleimide derivative of choice derived from SMCC), and wherein R' is a water solubilizing entity, such as an aminopolycarboxylate (e.g., DTPA) or a derivative of piperazine. The derivatization of CPT or its analog as an ester at the C-20 hydroxyl, through the use of an amino acid or a dipeptide as enumerated in the embodiments described already, results in an amino group which is available for activation. The amino group can be converted to an isothiocyanato group by methods well known in the art; the latter is linked to the side chain amino group of the internal lysine moiety of the peptide template described above. In this way, a water-solubilizing group and an antibody-reative group are added in a single step. Moreover, by modifying the peptide template to contain more than one central lysine or other side-chain-amine-containing amino acid, such as arginine, multiple chemotherapeutic drug moieties can be added.

It is contemplated that the above-mentioned approach can be useful in introducing 1 to 5, more preferably 1 to 2 chemotherapeutic drug moieties onto the linker.

In yet another preferred embodiment, a pH-sensitive intracellularly-cleavable moiety is used as a linker binding the targeting moiety to the chemotherapeutic moiety. An advantage with this approach is that intratumoral release of the chemotherapeutic moiety will not depend upon the extent of expression of specific enzymes for the breakage of the bonds of the intracellularly-cleavable moiety that links the targeting moiety to the chemotherapeutic moiety.

For example, the 20-hydroxyl group of CPT can be attached under acid catalysis to a pH-sensitive intracellularly-cleavable moiety comprising a dihydropyran moiety, a tetrahydrofuran moiety or an orthoester moiety which, in turn, comprises a thiol-reactive moiety (e.g., maleimide), and water solubilizing group (e.g., piperazine). See Chart 1. pH-sensitive intracellularly-cleavable moieties comprising a dihydropyran, tetrahydrofuran or an orthoester moiety all comprise an ether bond that is susceptible to cleavage under the acidic pH of intracellular compartments.

A linker with structure-1 in the chart below is used. In this example, the central piperazine portion will allow for water-solubility. The substituted dihydropyran at the 'left end' of the molecule is for coupling to the hydroxyl group(s) in CPT derivatives, while the maleimide at the 'right end' of the molecule is a prototypical thiol-reactive group for conjugating to disulfide-reduced antibody. Herein, 'CPT' is used as a general term, and can be CPT, 10-hydroxy-CPT, or SN-38, as shown in the Chart. In the case of 10-hydroxy-CPT and SN-38, derivatizations can be envisaged at both 10-hydroxy and 20-hydroxy positions. The bonding of CPT to the cross-linker is via a tetrahydropyran moiety. This bond is slowly cleaved at pH 4-6, but stable above pH 6 (Greene T W, Wuts P G M: *Protective groups in organic synthesis, second edition*; John Wiley & Sons: New York, 1991; pp 413-416.) This approach takes advantage of the acidic nature of intracellular compartment; generally about 5. (Poznansky M J and Juliano R L, *Pharmacol Rev* 36:277-336, 1984.) This acidic pH in intracellular compartments causes the release the drug intact from the antibody.

As mentioned above, tetrahydrofuranyl moieties are contemplated as integral parts of pH-sensitive intracellularly-cleavable moieties. (Greene T W, Wuts P G M: *Protective groups in organic synthesis, second edition*; John Wiley & Sons: New York, 1991; pp 267-269.) When the pH-sensitive intracellularly cleavable moiety comprises a tetrahydrofuranyl moiety, the cleavage of the CPT C20-oxygen-tetrahydrofuran bond cleaves faster than when a tetrahydropyranyl moiety is used.

Chart

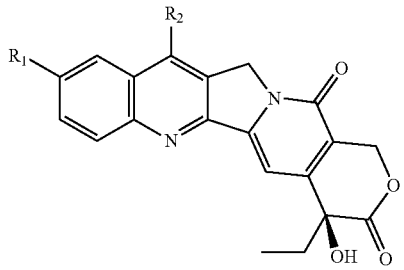

CPT: R$_1$ = R$_2$ = H
10-OH-CPT: R$_1$ = OH; R$_2$ = H
SN-38: R1 = OH; R$_2$ = ethyl

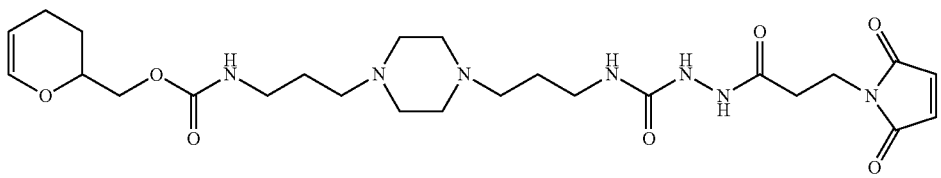

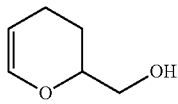

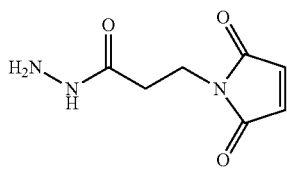

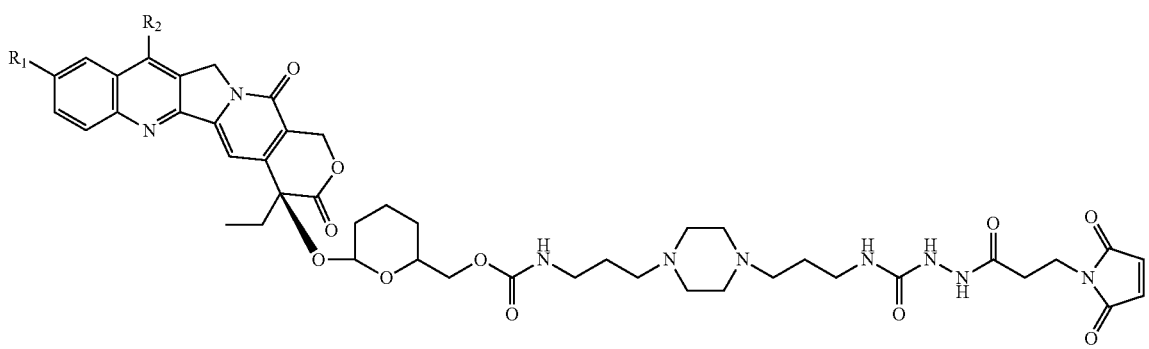

Suitable routes of administration of the immunoconjugates of the preferred embodiments of the present invention include, without limitation, oral, parenteral, rectal, transmucosal, intestinal administration, intramuscular, subcutaneous, intramedullary, intrathecal, direct intraventricular, intravenous, intravitreal, intraperitoneal, intranasal, or intraocular injections. The preferred routes of administration are parenteral. Alternatively, one may administer the compound in a local rather than systemic manner, for example, via injection of the compound directly into a solid tumor.

The present invention is illustrated by the following examples, without limiting the scope of the invention.

EXAMPLES

Example-1: Preparation of C-20-O—(N-'MCC') Glycinate Derivative of 10-Hydroxycamptothecin, where MCC is 4-(N-Maleimidomethyl)-Cyclohexane-1-Carbonyl Residue

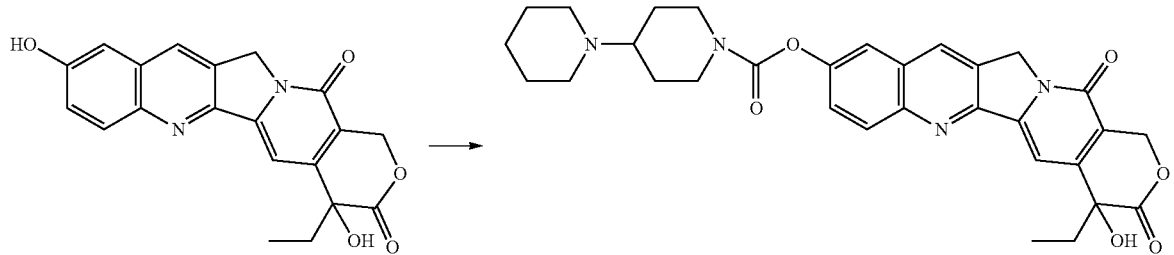

MW: 558 (electrospray MS)

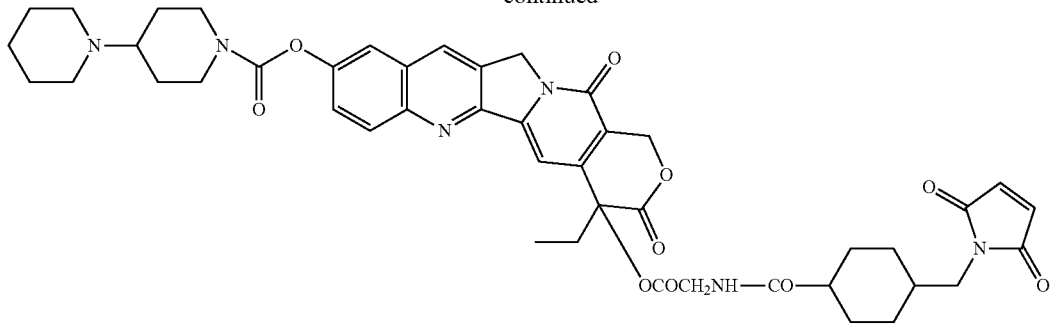

3

10-Hydroxycamptothecin (0.2081 g; 0.57 mmol) was dissolved in 20 mL of anhydrous dimethyl formamide (DMF) and 0.22 mL of diisopropylethylamine (DIEA). To this was added 0.1248 g (0.619 mmol) of 4-nitrophenyl chloroformate, and the reaction mixture was stirred under argon, at the room temperature, for 4 h. A solution of 4-piperidinopiperidine (0.2403 g) in 4 mL of DMF was added in one lot, and the mixture was stirred for another 2 h. Solvent removal furnished the crude product, which was purified by flash chromatography on silica gel (230-400 mesh) using methanol-dichloromethane gradient elution to obtain 52.8 mg of the intermediate 2. Electrospray mass spectrum showed a clean peak at m/e 559 (M+H) in the positive ion mode, and peaks at m/e 557 (M−H) and 593 (M+Cl) in the negative ion mode. The intermediate 2 (25 mg) was reacted with BOC-glycine (8.9 mg), N,N-dimethylaminopyridine (DMAP) (2 mg) and dicyclohexylcarbodiimide (DIC) (0.058 mL of 1 M solution in dichloromethane) in 10 mL of dichloromethane (DCM) for 18 h (room temperature, under argon). The reaction mixture was worked up and purified by flash chromatography to obtain C-20-O—(BOC)glycinate in ~50% yield. This product was reacted with a 10% DCM solution of trifluoroacetic acid (TFA), for 1-to-2 h, to obtain 20-O-glycinate derivative. The latter was derivatized with 1.2 molar equivalent of succinimidylmaleimidomethylcyclohexanecarboxylate (SMCC) and 1.5 equivalent of DIEA in DMF for ~3 h (room temperature, under argon). Solvent removal and flash chromatography resulted in the recovery of 7.8 mg of pure 3 as gummy solid. 3: Analytical HPLC ($C_{18}$ column, gradient elution using solution A changing to solution 'B' in 10 minutes at 3 mL/min, then maintained at 100% 'B' for 5 min.; 'A': 0.1% aq. TFA; 'B': 90% $CH_3CN$/0.1% TFA) showed single peak 9.48 min (absorbance at 360 nm). Electrospray mass spectrum showed mass peak at m/e 835 (M+H).

Example-2: Preparation of C-20-O—(N-'MCC') Glycinate Derivative of Irinotecan (CPT-11), where MCC is 4-(N-maleimidomethyl)-cyclohexane-1-carbonyl Residue Scheme-2

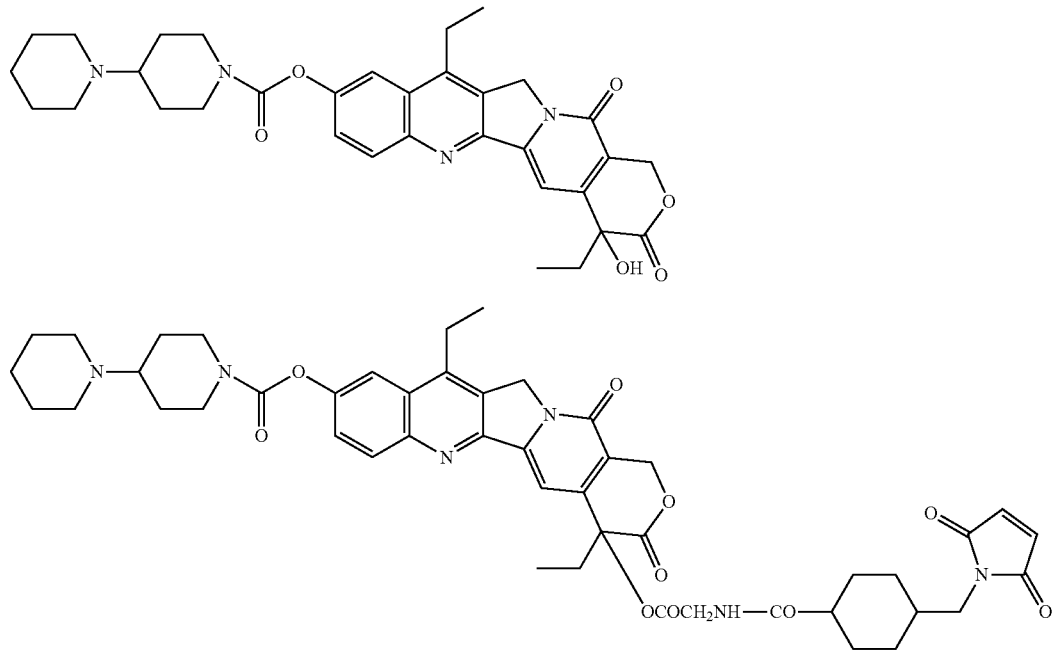

MW: 862 (electrospray MS)

Starting from CPT-11 (4), the product 5 was prepared in a 3-step procedure by reacting with BOC-glycine (purified product showed M+H at m/e 744 in electrospray mass spectrum), deprotection with TFA (M+H peak at m/e 644 in mass spectrum), and coupling to SMCC, as in Example-1. Product purifications were carried out as in Example-1. The final product 5 showed an intense peak at m/e 863 in the positive ion mode electrospray mass spectrum, and a clean peak in analytical HPLC at 9.69 min. Pure product 5 was obtained as a white solid, and was produced in 25 mg amount.

Example-3: Preparation of 10-Piperazinocarbonyloxy Camptothecin (6) and its Coupling to a Heterobifunctional Poly(Ethyleneglycol), Maleimide-PEG-NHS Example-4: General Procedure for Conjugating CPT Derivatives 3 or 5 or 7 with Monoclonal Antibodies The anibody was treated with a 20-to-40-fold molar excess of dithiothreitol and ethylene diamine tetraacetic acid (EDTA) (~5 mM final conc.) at pH 7.4, flushed with argon, and incubated for 45 min. at 37° C. The cooled contents were then purified on two successive 3-mL columns of Sephadex G50/80 in 50 mM sodium acetate-150 mM sodium chloride pH 5.3 ("ABS buffer") under centrifuged elution conditions (centrifuged SEC). The eluate was analyzed for protein concentration using absorbance at 280 nm, and thiol content by Ellman's assay. The reduced antibodies contained 7-to-9 thiol groups. The reduced antibody was reacted with a 20-fold molar excess of the CPT derivative in DMF such that the final concentration of DMF in the

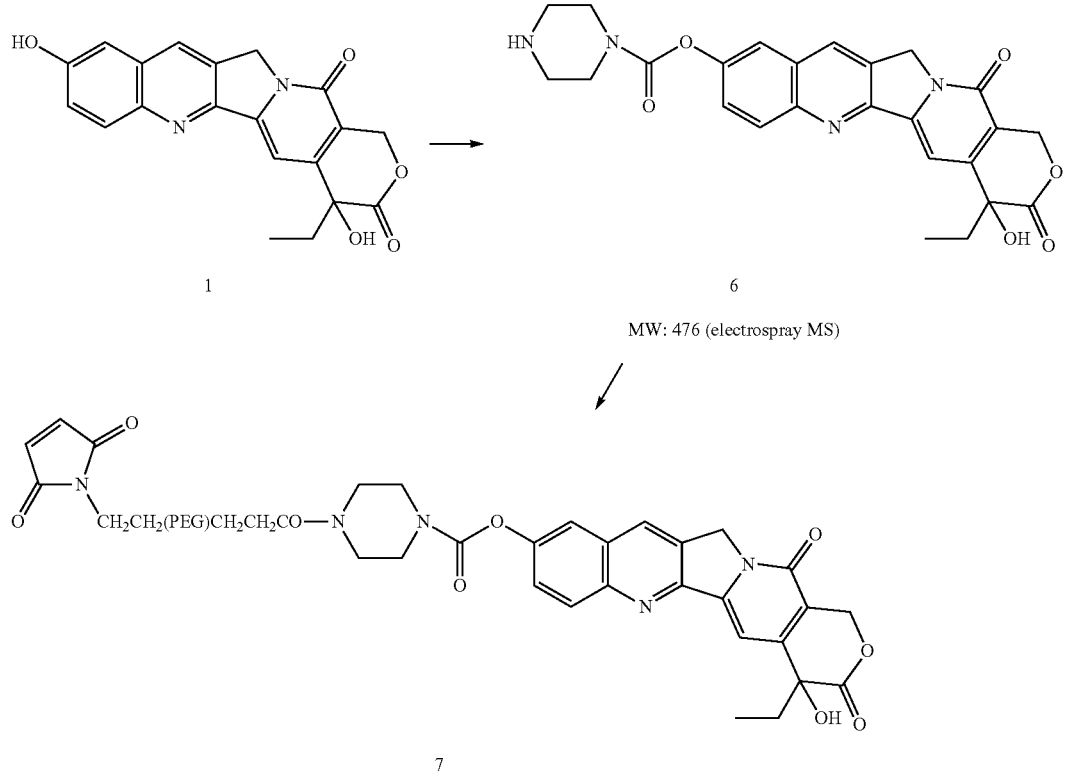

Scheme-3

MW: 476 (electrospray MS)

The preparation of the intermediate 6 in the Scheme-3 above was achieved along the lines of the preparation of 2 in Scheme-1 by using piperazine in place of piperidinopiperidine. After flash chromatographic purification, 6 was obtained in 43.3% yield (orange solid). Electrospray mass spectrum showed M+H at m/e 477 and M−H (negative ion mode) at m/e 475. For the preparation of 7, the precursor 6 was mixed with 0.5 molar equivalent of poly(ethylene glycol-α-N-hydroxysuccinimidyl propionate, β-maleimide, MW 3400 (obtained from Shearwater Polymers, Huntsville, Ala.) in DMF, and incubated for 30 min. The reaction mixture was used as such without purification. The molar content of the activated CPT was considered equal to that of the limiting PEG reagent used.

conjugation mixture was 5% v/v, and incubated on ice (~4° C.) for 20-to-30 min. Two successive centrifuged-SEC purifications on Sephadex G50/80 in ABS buffer, followed by passing the eluate through a hydrophobic column to remove non-covalently bound CPT derivative, furnished the final conjugate. In the case of conjugates using 7, additional purification by ultrafiltration on a30K MWCO centifugal filter proved necessary. In all the conjugate preparations, the reaction mixtures as well as the purified conjugates were clear solutions, indicating that the water-soluble nature of CPT derivatives used. Analysis by SE-HPLC was carried out on an analytical SEC250 column, fitted with a guard column and an in-line absorbance detector, using 0.2 M sodium phosphate pH 6.8 as eluent and 1 mL/min as the flow rate. The product was also analyzed by spectrophotometric absorbance scan in the 260-540 nm region. Absorbance at 360 nm was correlated with that obtained with a CPT-11 standard to determine the CPT concentration in the conjugate. Absorbance at 280 nm, corrected for spillover from CPT derivative, was used to calculate the antibody concentration. This way, the CPTderivative-to-IgG molar ratio was determined. The product was mixed with 10% v/v of 1 M sucrose, aliquoted in 1 mg and 0.1 mg lots, and lyophilized. The lyophilized preparations were stored in freezer after argon flush.

Example-5: MAb Conjugates of a Derivative of 10-hydroxy CPT, 3

The conjugates were prepared as described in Example-4. The following are the data pertaining to various conjugates. Murine LL2 (anti-CD-22 MAb) conjugate of 3: SE-HPLC analysis, with absorbance detection set at the CPT absorbance maximum of 360 nm, showed predominantly a single peak eluting at the retention time of unmodified LL2, the latter analyzed under the same conditions with detection set at 280 nm. Aggregate content: 1.6%. Molar substitution of 3 in the conjugate (i.e. 3-to-IgG ratio) was found to be 8.3 by absorbance scan, and 6 by MALDI mass spectral analysis.
Murine LL1 (anti-CD-74 MAb) conjugate of 3: SE-HPLC analysis, with absorbance detection set at the CPT absorbance maximum of 360 nm, showed predominantly a single peak eluting at the retention time of unmodified LL1, the latter analyzed under the same conditions with detection set at 280 nm. Aggregate content: 2.5%. Molar substitution of 3 in the conjugate (i.e. 3-to-IgG ratio) was found to be 7.9 by absorbance scan.
Murine RS7 (anti-EGP-1 MAb) conjugate of 3: SE-HPLC analysis, with absorbance detection set at the CPT absorbance maximum of 360 nm, showed predominantly a single peak eluting at the retention time of unmodified RS7, the latter analyzed under the same conditions with detection set at 280 nm. Aggregate content: 1.4%. Molar substitution of 3 in the conjugate (i.e. 3-to-IgG ratio) was found to be 6.9 by absorbance scan.
Humanized LL2 (anti-CD-22 MAb) conjugate of 3: SE-HPLC analysis, with absorbance detection set at the CPT absorbance maximum of 360 nm, showed predominantly a single peak eluting at the retention time of unmodified hLL2, the latter analyzed under the same conditions with detection set at 280 nm. Aggregate content: 0%. Molar substitution of 3 in the conjugate (i.e. 3-to-IgG ratio) was found to be 7.1 by absorbance scan.
Humanized AFP31 (anti-AFP MAb) conjugate of 3: SE-HPLC analysis, with absorbance detection set at the CPT absorbance maximum of 360 nm, showed predominantly a single peak eluting at the retention time of unmodified hAFP31, the latter analyzed under the same conditions with detection set at 280 nm. Aggregate content: 0%. Molar substitution of 3 in the conjugate (i.e. 3-to-IgG ratio) was found to be 8.0 by absorbance scan.

Example-6: MAb Conjugates of a Derivative of CPT-11, 5

The conjugates were prepared as described in Example-4. The following are the data pertaining to various conjugates. Murine LL2 (anti-CD-22 MAb) conjugate of 5: SE-HPLC analysis, with absorbance detection set at the CPT absorbance maximum of 360 nm, showed predominantly a single peak eluting at the retention time of unmodified LL2, the latter analyzed under the same conditions with detection set at 280 nm. Aggregate content: 2.2%. Molar substitution of 5 in the conjugate (i.e. 5-to-IgG ratio) was found to be 9.7 by absorbance scan.
Murine LL1 (anti-CD-74 MAb) conjugate of 5: SE-HPLC analysis, with absorbance detection set at the CPT absorbance maximum of 360 nm, showed a peak (91.2%) eluting at the retention time of unmodified LL1, the latter analyzed under the same conditions with detection set at 280 nm. Aggregate content: 8.8%. Molar substitution of 5 in the conjugate (i.e. 5-to-IgG ratio) was found to be 10.9 by absorbance scan.
Murine MN-14 (anti-CEA MAb) conjugate of 5: SE-HPLC analysis, with absorbance detection set at the CPT absorbance maximum of 360 nm, showed a peak eluting at the retention time of unmodified MN-14, the latter analyzed under the same conditions with detection set at 280 nm. Aggregate content: 9.3%. Molar substitution of 5 in the conjugate (i.e. 5-to-IgG ratio) was found to be 10.0 by absorbance scan.
Humanized LL2 (anti-CD-22 MAb) conjugate of 5: SE-HPLC analysis, with absorbance detection set at the CPT absorbance maximum of 360 nm, showed predominantly a single peak eluting at the retention time of unmodified hLL2, the latter analyzed under the same conditions with detection set at 280 nm. Aggregate content: 0%. Molar substitution of 5 in the conjugate (i.e. 5-to-IgG ratio) was found to be 8.4 by absorbance scan.

Example-7: MAb Conjugates of a PEG-Derivative of 10-hydroxy CPT, 7

The conjugates were prepared as described in Example-4. The following are the data pertaining to various conjugates. Murine LL2 (anti-CD-22 MAb) conjugate of 7: SE-HPLC analysis, with absorbance detection set at the CPT absorbance maximum of 360 nm, showed a peak (83%) eluting near the retention time of unmodified LL2, along with aggregate content of 16.3%. Molar substitution of 7 in the conjugate (i.e. 7-to-IgG ratio) was found to be 8.0 by absorbance scan.
Murine LL1 (anti-CD-74 MAb) conjugate of 7: SE-HPLC analysis, with absorbance detection set at the CPT absorbance maximum of 360 nm, showed a peak (94%) eluting near the retention time of unmodified LL1, along with aggregate content of 6.0%. Molar substitution of 7 in the conjugate (i.e. 7-to-IgG ratio) was found to be 8.1 by absorbance scan.
Murine RS7 (anti-EGP-1 MAb) conjugate of 7: SE-HPLC analysis, with absorbance detection set at the CPT absorbance maximum of 360 nm, showed a peak eluting near the retention time of unmodified RS7, along with aggregate content of 4.5%. Molar substitution of 7 in the conjugate (i.e. 7-to-IgG ratio) was found to be 8.0 by absorbance scan.

Example-8: A General Method for the Preparation of Aminopolycarboxylate-Appended Bifunctional CPT(s), Suitable for Conjugation to Lysine or Thiol Group on an Antibody The general approach is shown in Scheme-4. Briefly, CPT and 10-hydroxy-CPT were converted to the corresponding C-20-O-glycinate by the method of Singer (supra). In a parallel synthesis, isothiocyanatobenzyl DTPA penta t-butyl ester was generated from the corresponding amine precursor, and then coupled to S-trityl cysteine. Flash chromatographic purification gave the intermediate 11 (mass spectrum: M+Na m/e 1207; M−H: 1183).

Intermediate 11 was then coupled to the CPT derivative 9. TFA-mediated deprotection of t-butyl groups of carboxylates and S-trityl group, using scavengers to capture t-butyl cation, then furnished the DTPA-appended bifunctional CPT derivative (R=H or OH), suitable for conjugating to maleimide groups appended to IgG.

The thiol group is also derivatized with excess divinylsulfone to produce an intermediate possessing a vinylsulfone group, which is suitable for conjugating to thiol groups of disulfide-reduced antibodies.

Intermediate 13 is another example of an aminopolycarboxylate which can be used in place of isothiocyanatobenzyl DTPA in these transformations.

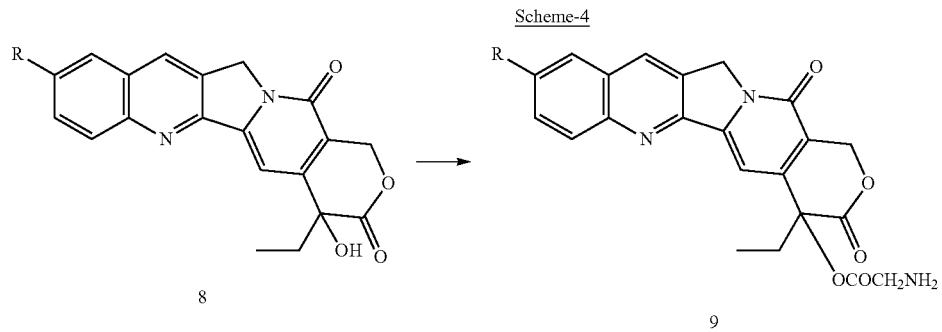

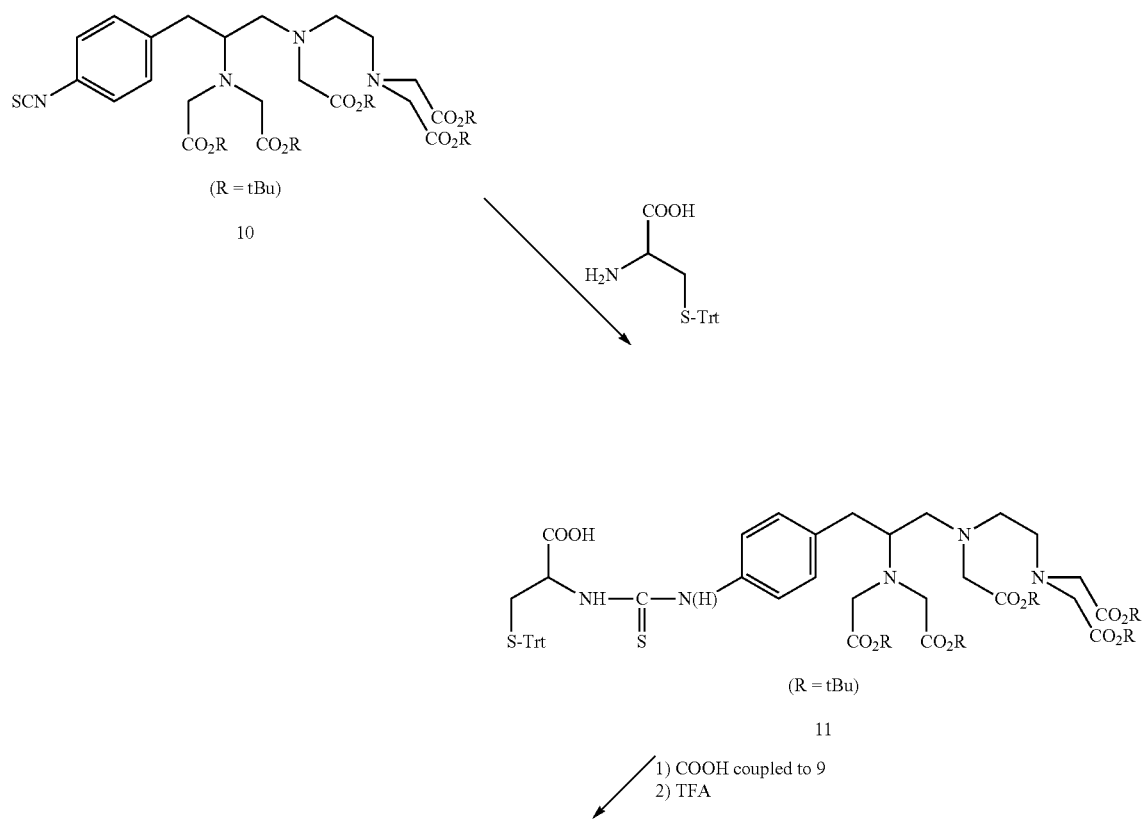

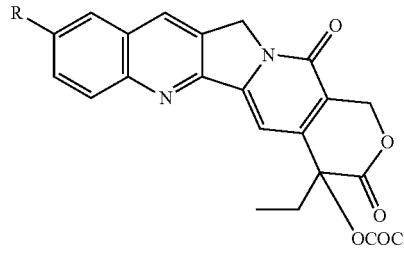
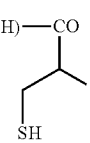
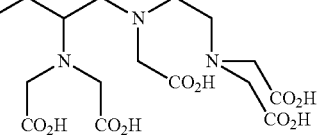

12

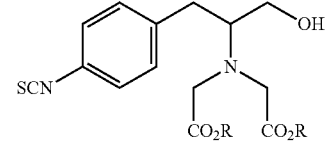

(R = tBu)

13

(R = H for CPT or OH for 10-OH-CPT)

Example-9: Method for the Preparation of SN-38 Conjugates

SN-38 is the active drug which is metabolically converted, in vivo, from the prodrug CPT-11 (Liehr, Giovanella, Verschraegen (eds) (supra). SN-38 is the active chemotherapeutic drug which is 3 orders of magnitude more potent than CPT-11 in inhibiting topoisomerase I activity. Bifunctional SN-38, suitable for antibody conjugation is simply prepared as follows: [CPT-11]-20-O-valinate, with its valine N-terminus protected as BOC, is selectively cleaved at its C-10-carbamate using one equivalent of a base such as hydroxide. "Anhydrous hydroxide", such as that derived from 2 equivalents of potassium t-butoxide and one equivalent of water (Gassman and Schenk, *J. Org. Chem.*, 42:918-920 (1977)), is advantageously used for this purpose. The valinate ester of CPT has been shown to be stable to 1 equivalent of 1N aq. sodium hydroxide for at least 1 hour. This way, the C-10-carbamate is selectively cleaved. The amino group of the valine moiety is then converted to isothiocyanate, and coupled to the peptide template MCC-Gly-Lys-Lys(R')—NH₂. Alternatively, SN-38 itself is derivatized by first protecting the C10-hydroxyl group as an an acid sensitive derivative, such as methoxytrityl derivative. The C20-hydroxyl group is then converted to the valinate ester. At this point, the methoxytrityl group at C-10 position is removed. A different option would be to first prepare the 20-valinate ester (or any other ester) derivative of SN-38 via protection of C-10 hydroxyl as the corresponding 'BOC' ester, derivatization of 20-hydroxyl group, and deprotection. This is then followed by treatment with trimethylsilyl chloride to derivatize both C-10 hydroxyl and the amino group of the ester at C-20, reacting with amine-reactive heterobifunctional crosslinker, such as maleimide-PEG-NHS, and deprotecting trimethylsilyl group at C-10 position.

The above approach is not limited to CPT derivatives, and is applicable to other hydrophobic drugs such as paclitaxel, geldanamycin, and the like.

From the foregoing description, one skilled in the art can easily ascertain the essential characteristics of this invention, and without departing from the spirit and scope thereof, can make various changes and modifications of the invention to adapt it to various usage and conditions without undue experimentation. All patents, patent applications and publications cited herein are incorporated by reference in their entirety.

The CDRs of the heavy chain variable region of the humanized anti-AFP Mab comprises CDR1 comprising an amino acid sequence of SYVIH (SEQ ID NO:1); CDR2 comprising an amino acid sequence of YIHPYNGGT-KYNEKFKG (SEQ ID NO:2) and CDR3 comprising an amino acid sequence of SGGGDPFAY (SEQ ID NO:3) and the CDRs of the light chain variable region of the humanized anti-AFP Mab comprises CDR1 comprising an amino acid sequence of KASQDINKYIG (SEQ ID NO:4), CDR2 comprising an amino acid sequence of YTSALLP (SEQ ID NO:5) and CDR3 comprising an amino acid sequence of LQYDDLWT (SEQ ID NO:6).

The CDRs of the light chain variable region of the humanized RS7 comprises CDR1 comprising an amino acid sequence of KASQDVSIAVA (SEQ ID NO:7), SASYRYT (SEQ ID NO:8) and QQHYITPLT (SEQ ID NO:9) and the CDRs of the heavy chain variable region of the humanized anti-CD20 MAb comprises sequence comprising CDR1 comprising an amino acid sequence of NYGMN (SEQ ID NO:10), CDR2 comprising an amino acid sequence of WINTYTGEPTYTDDFKG (SEQ ID NO:11) and CDR3 comprising an amino acid sequence of GGFGSSYWYFDV (SEQ ID NO:12).

The light chain variable region of the humanized LL1 mAb comprises CDRs of a light chain variable region of a murine anti-CD74 mAb, that comprises CDR1 comprising an amino acid sequence RSSQSLVHRNGNTYLH (SEQ ID NO:13), CDR2 comprising an amino acid sequence TVS-NRFS (SEQ ID NO:14), and CDR3 comprising an amino acid sequence SQSSHVPPT (SEQ ID NO:15), and the heavy chain variable region of the humanized mAb comprises CDRs of a heavy chain variable region of a murine anti-CD74 mAb, that comprises CDR1 comprising an amino acid sequence NYGVN (SEQ ID NO:16), CDR2 comprising an amino acid sequence WINPNTGEPTFDDDFKG (SEQ ID NO:17), and CDR3 comprising an amino acid sequence SRGKNEAWFAY (SEQ ID NO:18).

The CDRs of the light chain variable region of the humanized PAM4 MAb comprise CDR1 comprising an amino acid sequence of SASSSVSSSYLY (SEQ ID NO:19); CDR2 comprising an amino acid sequence of STSNLAS (SEQ ID NO:20); and CDR3 comprising an amino acid sequence of HQWNRYPYT (SEQ ID NO:21); and the CDRs of the heavy chain variable region of the humanized PAM4 MAb comprise CDR1 comprising an amino acid sequence of SYVLH (SEQ ID NO:22); CDR2 comprising an amino acid sequence of YINPYNDGTQYNEKFKG (SEQ ID NO:23) and CDR3 comprising an amino acid sequence of GFGGSYGFAY (SEQ ID NO:24).

The CDRs of the light chain variable region of the humanized anti-CSAp MAb comprises CDR1 comprising an amino acid sequence of RSSQSIVHSNGNTYLE (SEQ ID NO:25); CDR2 comprising an amino acid sequence of KVSNRF (SEQ ID NO:26) and CDR3 comprising an amino acid sequence of FQGSRVPYT (SEQ ID NO:27); and the CDRs of the heavy chain variable region of the humanized anti-CSAp MAb comprises CDR1 comprising an amino acid sequence of EYVIT (SEQ ID NO:28); CDR2 comprising an amino acid sequence of EIYPGSGSTSYNEKFK (SEQ ID NO:29) and CDR3 comprising an amino acid sequence of EDL (SEQ ID NO:30).

What is claimed is:

1. An immunoconjugate consisting essentially of:
   a) an antibody or an antigen-binding fragment thereof, wherein said antibody or fragment thereof binds to a tumor-associated antigen CEACAM5; and
   b) six or more molecules of SN-38 covalently attached to the antibody or antibody fragment; and
   c) a linker attaching the SN-38 to the antibody or fragment thereof.

2. The immunoconjugate of claim 1, wherein the linker moiety comprises a maleimide moiety that binds to a reduced sulfhydryl on the antibody or antibody fragment.

3. The immunoconjugate of claim 1, wherein the linker is an intracellularly cleavable linker.

4. The immunoconjugate of claim 3, wherein the linker comprises a peptide moiety that is cleavable by a lysosomal enzyme.

5. The immunoconjugate of claim 1, wherein 7 to 12 SN-38 are attached to the antibody or antibody fragment.

6. The immunoconjugate of claim 1, wherein the antibody is a chimeric, humanized or human antibody.

7. The immunoconjugate of claim 1, wherein the antibody is hMN-14.

8. The immunoconjugate of claim 1, wherein the antibody fragment is selected from the group consisting of a Fab, Fab', F(ab)$_2$, F(ab)$_2$ and scFv antibody fragment.

9. The immunoconjugate according to claim 1, wherein said antibody comprises the heavy chain variable region CDR sequences CDR1 (TYWMS, SEQ ID NO:36), CDR2 (EIHPDSSTINYAPSLKD, SEQ ID NO:37) and CDR3 (LYFGFPWFAY, SEQ ID NO:38) and light chain variable region CDR sequences CDR1 (KASQDVGTSVA, SEQ ID NO:39), CDR2 (WTSTRHT, SEQ ID NO:40) and CDR3 (QQYSLYRS, SEQ ID NO:41).

10. The immunoconjugate of claim 1, wherein the antibody is a humanized antibody.

* * * * *

UNITED STATES PATENT AND TRADEMARK OFFICE
CERTIFICATE OF CORRECTION

PATENT NO.         : 10,280,220 B2  
APPLICATION NO.    : 15/174304  
DATED              : May 7, 2019  
INVENTOR(S)        : Serengulam V. Govindan Page 1 of 1

It is certified that error appears in the above-identified patent and that said Letters Patent is hereby corrected as shown below:

On the Title Page

Item (73), should read:
--Immunomedics, Inc., Morris Plains, NJ (US)--

Signed and Sealed this
Thirty-first Day of March, 2020

Andrei Iancu
*Director of the United States Patent and Trademark Office*

```
                            SEQUENCE LISTING

<160> NUMBER OF SEQ ID NOS: 41

<210> SEQ ID NO 1
<211> LENGTH: 5
<212> TYPE: PRT
<213> ORGANISM: Mus musculus

<400> SEQUENCE: 1

Ser Tyr Val Ile His
1               5

<210> SEQ ID NO 2
<211> LENGTH: 17
<212> TYPE: PRT
<213> ORGANISM: Mus musculus

<400> SEQUENCE: 2

Tyr Ile His Pro Tyr Asn Gly Gly Thr Lys Tyr Asn Glu Lys Phe Lys
1               5                   10                  15

Gly

<210> SEQ ID NO 3
<211> LENGTH: 9
<212> TYPE: PRT
<213> ORGANISM: Mus musculus

<400> SEQUENCE: 3

Ser Gly Gly Gly Asp Pro Phe Ala Tyr
1               5

<210> SEQ ID NO 4
<211> LENGTH: 11
<212> TYPE: PRT
<213> ORGANISM: Mus musculus

<400> SEQUENCE: 4

Lys Ala Ser Gln Asp Ile Asn Lys Tyr Ile Gly
1               5                   10

<210> SEQ ID NO 5
<211> LENGTH: 7
<212> TYPE: PRT
<213> ORGANISM: Mus musculus

<400> SEQUENCE: 5

Tyr Thr Ser Ala Leu Leu Pro
1               5
```

```
<210> SEQ ID NO 6
<211> LENGTH: 8
<212> TYPE: PRT
<213> ORGANISM: Mus musculus

<400> SEQUENCE: 6

Leu Gln Tyr Asp Asp Leu Trp Thr
1               5

<210> SEQ ID NO 7
<211> LENGTH: 11
<212> TYPE: PRT
<213> ORGANISM: Mus musculus

<400> SEQUENCE: 7

Lys Ala Ser Gln Asp Val Ser Ile Ala Val Ala
1               5                   10

<210> SEQ ID NO 8
<211> LENGTH: 7
<212> TYPE: PRT
<213> ORGANISM: Mus musculus

<400> SEQUENCE: 8

Ser Ala Ser Tyr Arg Tyr Thr
1               5

<210> SEQ ID NO 9
<211> LENGTH: 9
<212> TYPE: PRT
<213> ORGANISM: Mus musculus

<400> SEQUENCE: 9

Gln Gln His Tyr Ile Thr Pro Leu Thr
1               5

<210> SEQ ID NO 10
<211> LENGTH: 5
<212> TYPE: PRT
<213> ORGANISM: Mus musculus

<400> SEQUENCE: 10

Asn Tyr Gly Met Asn
1               5

<210> SEQ ID NO 11
<211> LENGTH: 17
<212> TYPE: PRT
<213> ORGANISM: Mus musculus

<400> SEQUENCE: 11

Trp Ile Asn Thr Tyr Thr Gly Glu Pro Thr Tyr Thr Asp Asp Phe Lys
1               5                   10                  15

Gly

<210> SEQ ID NO 12
<211> LENGTH: 12
<212> TYPE: PRT
<213> ORGANISM: Mus musculus

<400> SEQUENCE: 12

Gly Gly Phe Gly Ser Ser Tyr Trp Tyr Phe Asp Val
1               5                   10
```

<210> SEQ ID NO 13
<211> LENGTH: 16
<212> TYPE: PRT
<213> ORGANISM: Mus musculus

<400> SEQUENCE: 13

Arg Ser Ser Gln Ser Leu Val His Arg Asn Gly Asn Thr Tyr Leu His
1               5                   10                  15

<210> SEQ ID NO 14
<211> LENGTH: 7
<212> TYPE: PRT
<213> ORGANISM: Mus musculus

<400> SEQUENCE: 14

Thr Val Ser Asn Arg Phe Ser
1               5

<210> SEQ ID NO 15
<211> LENGTH: 9
<212> TYPE: PRT
<213> ORGANISM: Mus musculus

<400> SEQUENCE: 15

Ser Gln Ser Ser His Val Pro Pro Thr
1               5

<210> SEQ ID NO 16
<211> LENGTH: 5
<212> TYPE: PRT
<213> ORGANISM: Mus musculus

<400> SEQUENCE: 16

Asn Tyr Gly Val Asn
1               5

<210> SEQ ID NO 17
<211> LENGTH: 17
<212> TYPE: PRT
<213> ORGANISM: Mus musculus

<400> SEQUENCE: 17

Trp Ile Asn Pro Asn Thr Gly Glu Pro Thr Phe Asp Asp Asp Phe Lys
1               5                   10                  15

Gly

<210> SEQ ID NO 18
<211> LENGTH: 11
<212> TYPE: PRT
<213> ORGANISM: Mus musculus

<400> SEQUENCE: 18

Ser Arg Gly Lys Asn Glu Ala Trp Phe Ala Tyr
1               5                   10

<210> SEQ ID NO 19
<211> LENGTH: 12
<212> TYPE: PRT
<213> ORGANISM: Mus musculus

<400> SEQUENCE: 19

Ser Ala Ser Ser Ser Val Ser Ser Ser Tyr Leu Tyr
1               5                   10

<210> SEQ ID NO 20
<211> LENGTH: 7
<212> TYPE: PRT
<213> ORGANISM: Mus musculus

<400> SEQUENCE: 20

Ser Thr Ser Asn Leu Ala Ser
1               5

<210> SEQ ID NO 21
<211> LENGTH: 9
<212> TYPE: PRT
<213> ORGANISM: Mus musculus

<400> SEQUENCE: 21

His Gln Trp Asn Arg Tyr Pro Tyr Thr
1               5

<210> SEQ ID NO 22
<211> LENGTH: 5
<212> TYPE: PRT
<213> ORGANISM: Mus musculus

<400> SEQUENCE: 22

Ser Tyr Val Leu His
1               5

<210> SEQ ID NO 23
<211> LENGTH: 17
<212> TYPE: PRT
<213> ORGANISM: Mus musculus

<400> SEQUENCE: 23

Tyr Ile Asn Pro Tyr Asn Asp Gly Thr Gln Tyr Asn Glu Lys Phe Lys
1               5                   10                  15

Gly

<210> SEQ ID NO 24
<211> LENGTH: 10
<212> TYPE: PRT
<213> ORGANISM: Mus musculus

<400> SEQUENCE: 24

Gly Phe Gly Gly Ser Tyr Gly Phe Ala Tyr
1               5                   10

<210> SEQ ID NO 25
<211> LENGTH: 16
<212> TYPE: PRT
<213> ORGANISM: Mus musculus

<400> SEQUENCE: 25

Arg Ser Ser Gln Ser Ile Val His Ser Asn Gly Asn Thr Tyr Leu Glu
1               5                   10                  15

<210> SEQ ID NO 26
<211> LENGTH: 7
<212> TYPE: PRT
<213> ORGANISM: Mus musculus

<400> SEQUENCE: 26

Lys Val Ser Asn Arg Phe Ser
1               5

```
<210> SEQ ID NO 27
<211> LENGTH: 9
<212> TYPE: PRT
<213> ORGANISM: Mus musculus

<400> SEQUENCE: 27

Phe Gln Gly Ser Arg Val Pro Tyr Thr
1               5

<210> SEQ ID NO 28
<211> LENGTH: 5
<212> TYPE: PRT
<213> ORGANISM: Mus musculus

<400> SEQUENCE: 28

Glu Tyr Val Ile Thr
1               5

<210> SEQ ID NO 29
<211> LENGTH: 16
<212> TYPE: PRT
<213> ORGANISM: Mus musculus

<400> SEQUENCE: 29

Glu Ile Tyr Pro Gly Ser Gly Ser Thr Ser Tyr Asn Glu Lys Phe Lys
1               5                   10                  15

<210> SEQ ID NO 30
<211> LENGTH: 10
<212> TYPE: PRT
<213> ORGANISM: Mus musculus

<400> SEQUENCE: 30

Arg Ala Ser Ser Ser Val Ser Tyr Ile His
1               5                   10

<210> SEQ ID NO 31
<211> LENGTH: 7
<212> TYPE: PRT
<213> ORGANISM: Mus musculus

<400> SEQUENCE: 31

Ala Thr Ser Asn Leu Ala Ser
1               5

<210> SEQ ID NO 32
<211> LENGTH: 9
<212> TYPE: PRT
<213> ORGANISM: Mus musculus

<400> SEQUENCE: 32

Gln Gln Trp Thr Ser Asn Pro Pro Thr
1               5

<210> SEQ ID NO 33
<211> LENGTH: 5
<212> TYPE: PRT
<213> ORGANISM: Mus musculus

<400> SEQUENCE: 33

Ser Tyr Asn Met His
1               5
```

```
<210> SEQ ID NO 34
<211> LENGTH: 17
<212> TYPE: PRT
<213> ORGANISM: Mus musculus

<400> SEQUENCE: 34

Ala Ile Tyr Pro Gly Asn Gly Asp Thr Ser Tyr Asn Gln Lys Phe Lys
1               5                   10                  15
Gly

<210> SEQ ID NO 35
<211> LENGTH: 12
<212> TYPE: PRT
<213> ORGANISM: Mus musculus

<400> SEQUENCE: 35

Ser Thr Tyr Tyr Gly Gly Asp Trp Tyr Phe Asp Val
1               5                   10

<210> SEQ ID NO 36
<211> LENGTH: 5
<212> TYPE: PRT
<213> ORGANISM: Mus musculus

<400> SEQUENCE: 36

Thr Tyr Trp Met Ser
1               5

<210> SEQ ID NO 37
<211> LENGTH: 17
<212> TYPE: PRT
<213> ORGANISM: Mus musculus

<400> SEQUENCE: 37

Glu Ile His Pro Asp Ser Ser Thr Ile Asn Tyr Ala Pro Ser Leu Lys
1               5                   10                  15
Asp

<210> SEQ ID NO 38
<211> LENGTH: 10
<212> TYPE: PRT
<213> ORGANISM: Mus musculus

<400> SEQUENCE: 38

Leu Tyr Phe Gly Phe Pro Trp Phe Ala Tyr
1               5                   10

<210> SEQ ID NO 39
<211> LENGTH: 11
<212> TYPE: PRT
<213> ORGANISM: Mus musculus

<400> SEQUENCE: 39

Lys Ala Ser Gln Asp Val Gly Thr Ser Val Ala
1               5                   10

<210> SEQ ID NO 40
<211> LENGTH: 7
<212> TYPE: PRT
<213> ORGANISM: Mus musculus

<400> SEQUENCE: 40

Trp Thr Ser Thr Arg His Thr
1               5
```

```
<210> SEQ ID NO 41
<211> LENGTH: 8
<212> TYPE: PRT
<213> ORGANISM: Mus musculus

<400> SEQUENCE: 41

Gln Gln Tyr Ser Leu Tyr Arg Ser
1               5
```